US005798382A

United States Patent [19]

Kogami et al.

[11] Patent Number: 5,798,382

[45] Date of Patent: Aug. 25, 1998

[54] 2,3-DIHYDROBENZOFURAN DERIVATIVES, METHOD FOR PRODUCING THE SAME, AND USE THEREOF

[75] Inventors: Yuji Kogami; Naomi Aono; Daisuke Mochizuki, all of Shizuoka, Japan

[73] Assignee: Asahi Kasei Kogyo Kabushiki Kaisha, Osaka, Japan

[21] Appl. No.: 750,578

[22] PCT Filed: Jun. 9, 1995

[86] PCT No.: PCT/JP95/01160

§ 371 Date: Dec. 12, 1996

§ 102(e) Date: Dec. 12, 1996

[87] PCT Pub. No.: WO96/01816

PCT Pub. Date: Jan. 25, 1996

[30] Foreign Application Priority Data

Jul. 7, 1994 [JP] Japan .................................... 6-155898

[51] Int. Cl.$^6$ .......................... A61K 31/34; A61K 31/38; A61K 31/44

[52] U.S. Cl. .......................... 514/469; 514/337; 514/444; 549/60; 549/467; 546/284.1

[58] Field of Search .................................... 514/337, 444, 514/469; 546/284.1; 549/60, 467

[56] References Cited

U.S. PATENT DOCUMENTS 5,134,140 7/1992 Stack ....................................... 514/212

FOREIGN PATENT DOCUMENTS 0538080 4/1993 European Pat. Off. .
0679649 2/1995 European Pat. Off. .
9415930 7/1994 WIPO .

OTHER PUBLICATIONS

Chimie Therapeutique No. 3, pp. 259–270 (1973) (no translation available).
Izv. Akad. Nauk. Arn. SSR, Khim. Nauki 14, pp. 495–504 (1961) (no translation available).

*Primary Examiner*—Amelia Owens
*Attorney, Agent, or Firm*—Birch, Stewart, Kolasch & Birch, LLP

[57] ABSTRACT

Disclosed are a 2,3-dihydrobenzofuran derivative represented by formula (1) or a salt thereof, a method for producing the same, and use thereof:

$$\text{2,3-dihydrobenzofuran-2}^{*}\text{-}CH_2-N(R^1)-(CH_2)_n-NH-A-R^2 \quad (1)$$

wherein $R^1$ represents a hydrogen atom or a lower alkyl group; $R^2$ represents a naphthyl group, a pyridyl group, a furyl group or a thienyl group; n is an integer of from 2 to 6; A represents a carbonyl group or a sulfonyl group; and * represents an asymmetric carbon atom. The 2,3-dihydrobenzofuran derivatives of the present invention and the non-toxic salts thereof have a strong affinity for serotonin 1A receptors. Therefore, are useful as pharmaceutical composition containing the 2,3-dihydrobenzofuran derivatives and the non-toxic salts thereof are especially useful for treating a serotonergic neuron-related disease, such as anxiety, depression, eating disorder, high blood pressure, emesis (including emesis induced by motion sickness, space sickness, dizziness and drug, etc.) and the like.

8 Claims, No Drawings

2,3-DIHYDROBENZOFURAN DERIVATIVES, METHOD FOR PRODUCING THE SAME, AND USE THEREOF

BACKGROUND OF THE INVENTION

1. Technical field

The present invention relates to novel 2,3-dihydrobenzofuran derivatives, a method for producing the same, and use thereof.

The 2,3-dihydrobenzofuran derivatives and non-toxic salts thereof of the present invention have a high affinity for a serotonin 1A receptor and, therefore, are useful as pharmaceutical compositions for preventing and treating serotonergic neuron-related diseases, such as anxiety, depression, eating disorder, high blood pressure, emesis (including emesis induced by motion sickness, space sickness, dizziness and drug, etc.), and the like.

2. Background Art

In recent several years, it has been found that serotonin [5-hydroxytryptamine (5-HT)] as a neurotransmitter has correlations with various physiological phenomena, such as appetite, memory, thermoregulation, sleep, sexual behavior, anxiety, depression and stress [Glennon, R. A., J. Med. Chem., 30,1 (1987)].

It has been known that compounds acting on a 5-HT 1A receptor which is one of the serotonin-susceptive receptors are useful for preventing and treating anxiety, depression, eating disorder, high blood pressure, emesis (including emesis induced by motion sickness, space sickness, dizziness and drug, etc.), and the like. With respect to such compounds, a number of studies have been made and the results thereof have been reported [see, "Nippon Rinsho (Japanese Journal of Clinical Medicine)" vol. 47, special edition, pp. 1241–1248 (1989); J. P. Feighnev, W. F. Boyer, Psychopathology, 22, 21 (1989); P. R. Saxena, C. M. Villalon, TIPS, 11, 95 (1990); N. Matsuki, et al., Jpn. J. Pharmacol. Suppl., 58, 313 (1992); etc.].

It has been desired in the art to develop and provide a compound which is improved with respect to the above-mentioned pharmacological activities.

SUMMARY OF THE INVENTION

In these situations, the present inventors have made extensive and intensive studies, in which various types of compounds were synthesized and examined with respect to the pharmacological properties thereof. As a result, it has unexpectedly been found that novel 2,3-dihydrobenzofuran derivatives represented by formula (1) below exhibit an excellent affinity for a serotonin-susceptive 5-HT1A receptor and excellent pharmacological activities on such a receptor. The present invention has been completed, based on the above novel findings.

Accordingly, it is an object of the present invention to provide a compound exhibiting an excellent affinity for a serotonin-susceptive 5-HT1A receptor.

It is another object of the present invention to provide a pharmaceutical composition for treating a serotonergic neuron-related disease, which comprises the above-mentioned compound exhibiting excellent pharmacological activities against serotonergic neuron-related diseases.

It is still another object of the present invention to provide a method for treating a serotonergic neuron-related disease, which comprises administering to a patient suffering from a serotonergic neuron-related disease the above-mentioned pharmaceutical composition for treating a serotonergic neuron-related disease.

The foregoing and other objects, features and advantages of the present invention will be apparent to those skilled in the art from the following detailed description and appended claims.

DETAILED DESCRIPTION OF THE INVENTION

Accordingly, in one aspect of the present invention, there is provided a novel 2,3-dihydrobenzofuran derivative or a salt thereof, wherein the 2,3-dihydrobenzofuran derivative is represented by formula (1):

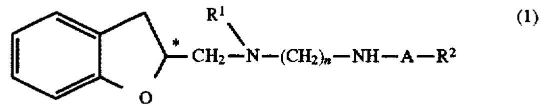

wherein $R^1$ represents a hydrogen atom or a lower alkyl group; $R^2$ represents a naphthyl group, a pyridyl group, a furyl group or a thienyl group; n is an integer of from 2 to 6; A represents a carbonyl group or a sulfonyl group; and * represents an asymmetric carbon atom.

In another aspect of the present invention, there is provided a method for producing a 2,3-dihydrobenzofuran derivative represented by formula (1) above or a salt thereof, which comprises reacting a compound represented by formula (2) [hereinafter, frequently referred to as "compound (2)"]:

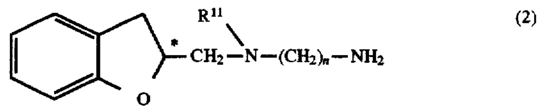

wherein $R^{11}$ represents an amino-protecting group or a lower alkyl group; and n and * are as defined for formula (1) above, with a compound represented by formula (3) [hereinafter, frequently referred to as "compound (3)"]:

$$X—A—R^2 \quad (3)$$

wherein X represents a leaving atom or group; and $R^2$ and A are as defined for formula (1) above, with the proviso that when $R^{11}$ in formula (2) is an amino-protecting group, a product obtained by the reaction of the compound represented by formula (2) with the compound represented by formula (3) is subsequently subjected to a treatment for eliminating the amino-protecting group so that a hydrogen atom is substituted therefor.

In another aspect of the present invention, there is provided a pharmaceutical composition, which is especially useful for treating a serotonergic neuron-related disease, and which comprises a therapeutically effective amount of a 2,3-dihydrobenzofuran derivative represented by formula (1) [hereinafter, frequently referred to as "compound (1)"] or a non-toxic salt thereof, and at least one pharmaceutically acceptable carrier, diluent or excipient.

In a further aspect of the present invention, there is provided a method for treating a serotonergic neuron-related disease, which comprises administering to a patient suffering from a serotonergic neuron-related disease a pharmaceutical composition comprising a therapeutically effective amount of compound (1) or a non-toxic salt thereof, and at least one pharmaceutically acceptable carrier, diluent or excipient.

In the present invention, a lower alkyl group means a straight chain or branched $C_1$–$C_4$ alkyl group. Specific examples of lower alkyl groups include methyl, ethyl, propyl, butyl, isopropyl, isobutyl, sec-butyl and tert-butyl.

Group A can be bonded to $R^2$ (which represents a naphthyl group, a pyridyl group, a furyl group or a thienyl group) at a carbon atom of an arbitrary position thereof. However, it is preferred that the group A-bonding position be the 1- or 2-position for a naphthyl group, the 2-, 3- or 4-position for a pyridyl group, the 2- or 3-position for a furyl group, and the 2- or 3-position for a thienyl group.

A compound represented by formula (4) [hereinafter, frequently referred to as "compound (4)"]

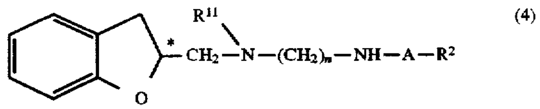

wherein $R^2$, $R^{11}$, A, n and * are as defined for formulae (1) and (2) above, can be obtained by the reaction of the above-mentioned compound (2) with compound (3). When $R^{11}$ of compound (4) is an amino-protecting group, a compound represented by formula (1) having a hydrogen atom as $R^1$ can be obtained from compound (4) by a conventional method for eliminating the amino-protecting group, as mentioned below. When $R^{11}$ of compound (4) is a lower alkyl group, compound (4) is obtained as a compound represented by formula (1) having a lower alkyl group as $R^1$.

Further, with respect to the obtained compound (1), when $R^1$ is a hydrogen atom, the compound may optionally be treated with an alkylating reagent mentioned below, to thereby replace the hydrogen atom with a lower alkyl group.

In the present invention, the amino-protecting group as $R^{11}$ of compound (2) is a group which protects the amino moiety (having $R^{11}$ bonded thereto) from undesired side reactions involving the amino moiety during the reaction of compound (2) with compound (3). With respect to the above-mentioned amino-protecting group, there is no particular limitation as long as the group can be easily eliminated from the obtained compound (4) without danger of the desired compound suffering unintended reactions. Examples of such amino-protecting groups include known amino-protecting groups, and reference can be made to the known literature [see, for example, Green, "Protective groups in organic synthesis", chapter 7, 1981; Green, Wuts, "Protective groups in organic synthesis" second edition, chapter 7, 1991]. Specific examples of amino-protecting groups include a tert-butoxycarbonyl group (Boc group), a benzyloxycarbonyl group (Cbz group), a 9-fluorenyloxycarbonyl group (Fmoc group), an ethoxy-carbonyl group, a methoxycarbonyl group, an acetyl group and a benzyl group.

Compound (2) used in the present invention can be prepared by, for example, reducing a compound represented by formula (5) [hereinafter, frequently referred to as "compound (5)"]:

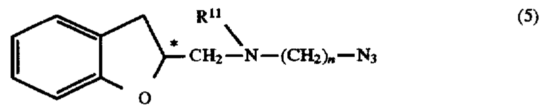

wherein $R^{11}$, n and * are as defined for formulae (1) and (2) above.

Specifically, the reduction of compound (5) can be conducted using an activated carbon-palladium as a catalyst, while introducing hydrogen gas to the reaction system. In this case, the catalyst is generally used in an amount of 1 to 20% by weight, preferably 5 to 10% by weight, based on the weight of compound (5). As an example of other methods for reducing compound (5), there can be mentioned a method in which lithium aluminum hydride, sodium borohydride or the like is used.

The reduction reaction of compound (5) is generally conducted in an inert medium. In the present invention, there is no particular limitation with respect to the inert medium as long as the medium is inert to the reaction system. Examples of inert media include dimethylformamide, dimethylacetamide, diethyl ether, tetrahydrofuran, methanol, ethanol and water. The amount of the inert medium is appropriately selected. For example, the inert medium can be used in a volume amount which is 5 to 100 times (v/w) the weight amount of compound (5). The reaction can be conducted under cooled or heated conditions, however, preferably at room temperature. The completion of reaction can be confirmed by observing the disappearance of the starting material. The reaction is generally completed within 30 minutes to 3 days. With respect to $R^{11}$ of compound (5), when $R^{11}$ is an amino-protecting group, undesirable elimination of the amino-protecting group may occur, during the reduction reaction, depending on the type of the amino-protecting group. Therefore, it is necessary to select an amino-protecting group which will not be eliminated during the reduction reaction. When the amino-protecting group is eliminated during the reduction reaction, it is necessary to introduce an amino-protecting group again.

Further, compound (5) can be obtained by reacting a compound represented by formula (6) [hereinafter, frequently referred to as "compound (6)"]:

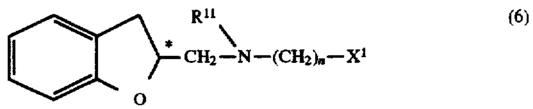

wherein $X^1$ represents a halogen atom or an organosulfonyloxy group; and $R^{11}$, n and * are as defined for formulae (1) and (2) above, with an azidating reagent.

The atom or group $X^1$ in the above-mentioned compound (6) means an atom or group which is eliminated from compound (6) with the azidating reagent during the reaction of compound (6) so that it is replaced by an azido group. Examples of atom or group $X^1$ include a halogen atom, such as a chlorine atom or a bromine atom, and an organosulfonyloxy group, such as a methanesulfonyloxy group and a p-toluenesulfonyloxy group.

Examples of azidating reagents include sodium azide and lithium azide. The azidating reagent can be used in an amount of from 1 to 10 equivalents, preferably 1 to 3 equivalents, per equivalent of compound (6).

The azidation reaction of compound (6) is generally conducted in an inert medium. With respect to the inert medium, there is no particular limitation as long as the medium is inert to the reaction system. Examples of inert media include dimethylformamide, dimethylacetamide, diethyl ether, tetrahydrofuran, chloroform and methylene chloride. Of these, dimethylformamide is especially preferred. The amount of the inert medium may be appropriately selected. For example, the inert medium is used in a volume amount which is 5 to 100 times (v/w) the weight amount of compound (6). Generally, the reaction is conducted under cooled or heated conditions, preferably under heated conditions. The completion of reaction can be confirmed by observing the disappearance of the starting material. The reaction is generally completed within 1 hour to 24 hours.

Compound (6) having an organosulfonyloxy group as $X^1$ can be obtained by reacting a compound represented by formula (7) [hereinafter, frequently referred to as "compound (7)"]:

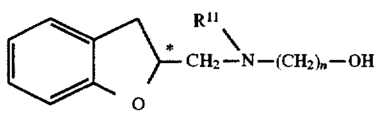

wherein $R^{11}$, n and * are as defined for formulae (1) and (2) above, with an organosulfonylating reagent, such as p-toluenesulfonyl chloride, p-toluenesulfonic anhydride or methanesulfonyl chloride.

The organosulfonylating reagent can be used in an amount within the range of from 1 to 10 equivalents, preferably 1 to 1.5 equivalents, per equivalent of compound (7). It is preferred that the reaction of compound (7) with a organosulfonylating reagent be conducted in the presence of a basic compound. Examples of basic compounds include known organic basic compounds, such as triethylamine, pyridine and 4-methylmorpholine; and known inorganic basic compounds, such as potassium carbonate, sodium carbonate and sodium hydrogencarbonate. The basic compound is used preferably in an equivalent or in a slightly excess amount relative to the amount of the sulfonylating reagent, e.g., about 1.5 equivalents per equivalent of the sulfonylating reagent.

The organosulfonylation reaction of compound (7) is generally conducted in an inert medium. With respect to the inert medium, there is no particular limitation as long as the medium is inert to the reaction system. Examples of inert media include, chloroform, methylene chloride, diethyl ether and tetrahydrofuran. The amount of the inert medium may be appropriately selected. For example, the inert medium is used in a volume amount which is 5 to 100 times (v/w) the weight amount of compound (7). The reaction is generally conducted at a temperature of from −25° C. to 40° C., preferably at room temperature. The completion of reaction can be confirmed by observing the disappearance of the starting material. Generally, the reaction is completed within 1 hour to 24 hours.

Compound (6) having a halogen atom as $X^1$ can be obtained by reacting compound (7) with a halogen-containing compound in the presence of a phosphine compound, such as triphenylphosphine. Examples of halogen-containing compounds include carbon tetrachloride and carbon tetrabromide. The halogen-containing compound is generally used in an amount of one equivalent or more or, if desired, may be used in an amount of 10 equivalents or more, per equivalent of compound (7). A phosphine compound (such as triphenylphosphine) may be used in an amount of from 1 to 10 equivalents, preferably 1 to 3 equivalents, per equivalent of compound (7).

The reaction of compound (7) with a halogen-containing compound in the presence of a phosphine compound is generally conducted in an inert medium. With respect to the inert medium, there is no particular limitation as long as the medium is inert to the reaction system. Examples of inert media include dimethylformamide, dimethylacetamide, diethyl ether and tetrahydrofuran. A halogen-containing compound can be used instead of the inert medium. The amount of the inert medium may be appropriately selected. For example, the inert medium is used in a volume amount which is 5 to 100 times (v/w) the weight amount of compound (7). The reaction can be conducted under cooled or heated conditions, however, preferably at room temperature. The completion of reaction can be confirmed by observing the disappearance of the starting material. Generally, the reaction is completed within 30 minutes to 1 day.

The above-mentioned compound (7) can be obtained by a conventional method. For example, compound (7) having a lower alkyl group as $R^{11}$ can be obtained from a compound represented by formula (8) [hereinafter, frequently referred to as "compound (8)"]:

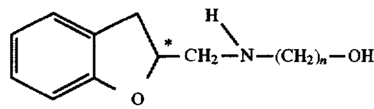

wherein n and * are as defined for formula (1) above, by introducing a lower alkyl group to compound (8) by the use of an alkylating reagent, such as methyl iodide, ethyl iodide, propyl iodide, isopropyl iodide and methyl bromide.

These alkylating reagents may be used in an amount within the range of from 1 to 10 equivalents, preferably 1 to 3 equivalents, per equivalent of compound (8). It is preferred that the reaction be conducted in the presence of a basic compound. Examples of basic compounds include known organic basic compounds, such as triethylamine, pyridine and 4-methylmorpholine; and known inorganic basic compounds, such as potassium carbonate, sodium carbonate and sodium hydrogencarbonate. The amount of the basic compound may be appropriately selected. For example, the basic compound is used in an amount of from 1 to 100 equivalents per equivalent of compound (8). The reaction is generally conducted in an inert medium. With respect to the inert medium, there is no particular limitation as long as the medium is inert to the reaction system. Examples of inert media include chloroform, methylene chloride, diethyl ether, tetrahydrofuran and acetonitrile. The amount of the inert medium may be appropriately selected. For example, the inert medium is used in a volume amount which is 5 to 100 times (v/w) the weight amount of compound (8). The reaction is generally conducted at a temperature of from −25° C. to 40° C., preferably at room temperature. The completion of reaction can be confirmed by observing the disappearance of the starting material. Generally, the reaction is completed within 1 hour to 3 days.

As an example of other methods for producing compound (7) having a lower alkyl group as $R^{11}$, there can be mentioned a method in which the above-mentioned compound (8) is reacted with an aldehyde reagent (such as an aqueous solution of formaldehyde, a solution of formaldehyde or acetaldehyde in an alcohol), followed by reduction using a reducing reagent (such as sodium borohydride or sodium cyanoborohydride), thereby obtaining compound (7) having a lower alkyl group as $R^{11}$. The aldehyde reagent may be used in an amount of from 1 to 10 equivalents, preferably 1 to 3 equivalents, per equivalent of compound (8). The reducing reagent may be used in an amount of from 1 to 10 equivalents, preferably 1 to 3 equivalents, per equivalent of compound (8).

The reaction of compound (8) with an aldehyde reagent and a reducing reagent is generally-conducted in an inert medium. In the present invention, there is no particular limitation with respect to the inert medium as long as the medium is inert to the reaction system. Examples of inert media include diethyl ether, tetrahydrofuran, methanol and ethanol. The amount of the inert medium may be appropriately selected. For example, the inert medium is used in a volume amount which is 5 to 100 times (v/w) the weight amount of compound (8).

Generally, the reaction is conducted at a temperature of from −25° C. to 40° C., preferably at room temperature. The completion of reaction can be confirmed by observing the disappearance of the starting material. Generally, the reaction is completed within 1 hour to 3 days.

Compound (7) having an amino-protecting group as $R^{11}$ can be produced by reacting compound (8) with a known protecting reagent, such as di-tert-butyl dicarbonate ($Boc_2O$), benzyloxycarbonyl chloride (Cbz-Cl) or 9-fluorenylmethyl chloroformate (Fmoc-Cl). The protecting reagent may be used in an amount of from 1 to 10 equivalents, preferably 1 to 3 equivalents, per equivalent of compound (8). It is preferred that the above-mentioned reaction be conducted in the presence of a basic compound. Examples of basic compounds include known organic basic compounds, such as triethylamine, pyridine and 4-methylmorpholine; and known inorganic basic compounds, such as potassium carbonate, sodium carbonate and sodium hydrogencarbonate. The basic compound can be used in an amount of from 1 to 100 equivalents per equivalent of compound (8); but preferably 1 to 5 equivalents, more preferably 1 to 1.5 equivalents, per equivalent of the protecting reagent.

Generally, the reaction of compound (8) with a protecting reagent is conducted in an inert medium. With respect to the inert medium, there is no particular limitation as long as the medium is inert to the reaction system. Examples of inert media include chloroform, methylene chloride, diethyl ether and tetrahydrofuran. The amount of the inert medium may be appropriately selected. For example, the inert medium is used in a volume amount which is 5 to 100 times (v/w) the weight amount of compound (8). Generally, the reaction is conducted at a temperature of from −25° C. to 40° C., preferably at room temperature. The completion of reaction can be confirmed by observing the disappearance of the starting material. Generally, the reaction is completed within 1 hour to 24 hours.

The above-mentioned compound (8) can be obtained by a conventional method. For example, compound (8) can be obtained by reacting a compound represented by formula (9) [hereinafter, frequently referred to as "compound (9)"]:

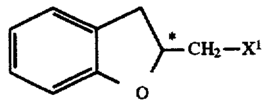

(9)

wherein $X^1$, n and * are as defined for formulae (1) and (6) above, with an amino alcohol, such as 2-aminoethanol, 3-amino-1-propanol, 4-amino-1-butanol, 5-amino-1-pentanol or 6-amino-1hexanol.

The amino alcohol can be used in an amount of one equivalent or more, preferably 3 to 5 equivalents, per equivalent of compound (9). The reaction is generally conducted in an inert medium. With respect to the inert medium, there is no particular limitation as long as the medium is inert to the reaction system. Examples of inert media include dimethylformamide, dimethylacetamide, diethyl ether, tetrahydrofuran, methanol, ethanol and acetonitrile. The amount of the inert medium may be appropriately selected. For example, the inert medium is used in a volume amount which is 5 to 100 times (v/w) the weight amount of compound (9).

The reaction of compound (1) with an amino alcohol can be conducted under cooled or heated conditions, preferably under heated conditions. The completion of reaction can be confirmed by observing the disappearance of the starting material. Generally, the reaction is completed within 3 hours to 2 days. It is preferred that the above-mentioned reaction be conducted in the presence of a basic compound. Examples of basic compounds include known organic basic compounds, such as triethylamine, pyridine and 4-methylmorpholine; and known inorganic basic compounds, such as potassium carbonate, sodium carbonate and sodium hydrogencarbonate. The amount of the basic compound may be appropriately selected. For example, the basic compound is used in an amount of from 1 to 100 equivalents per equivalent of compound (9). The above-mentioned basic compound may also function as an inert medium. The above-mentioned amino alcohol may be used in place of a basic compound or an inert medium.

With respect to the method for producing compound (9), reference can be made to Yakugaku Zasshi (Journal of Pharmacology) 88(5), 503–512 (1968) and Unexamined Japanese Patent Application Laid-Open Specification No. 3-188077. According to the methods disclosed therein, compound (9) can be synthesized from commercially available 2-allylphenol.

As an example of other methods for producing the above-mentioned compound (2), there can be mentioned a method in which compound (2) is produced by reacting a compound represented by formula (10) [hereinafter, frequently referred to as "compound (10)"]:

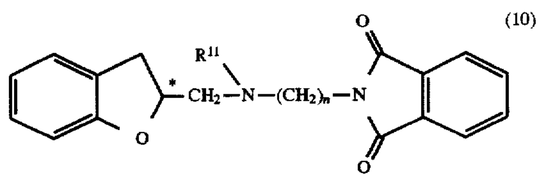

(10)

wherein $R^{11}$, n and * are as defined for formulae (1) and (2) above, with a hydrazine reagent to thereby eliminate the phthalimide group.

The hydrazine reagent can be used in an amount of from 1 to 10 equivalents, preferably 1 to 3 equivalents, per equivalent of compound (10). Examples of hydrazine reagents include hydrazine anhydride, 100% hydrazine hydrate and 80% aqueous hydrazine. The reaction is generally conducted in an inert medium. With respect to the inert medium, there is no particular limitation as long as the medium is inert to the reaction system. Examples of inert media include diethyl ether, tetrahydrofuran, methanol, ethanol and water. The amount of the inert medium may be appropriately selected. For example, the inert medium is used in a volume amount which is 5 to 100 times (v/w) the weight amount of compound (10). The reaction can be conducted under cooled or heated conditions, however, preferably at room temperature. The completion of reaction can be confirmed by observing the disappearance of the starting material. Generally, the reaction is completed within 30 minutes to 3 days.

The above-mentioned compound (10) can be obtained, for example, by reacting a compound represented by formula (11) [hereinafter, frequently referred to as "compound (11)"]:

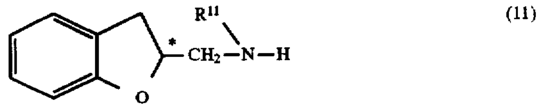

(11)

wherein $R^{11}$ and * are as defined for formulae (1) and (2) above, with an imide reagent, such as N-(2-bromoethyl) phthalimide, N-(3-bromopropyl)phthalimide or N-(4-bromobutyl)phthalimide. The imide reagent used in the reaction with compound (11) can be produced by a conventional method. Further, the imide reagent is commercially available and thus is readily obtained and used.

The imide reagent used in the reaction with compound (11) is generally used in an amount of one equivalent or more, preferably 1 to 5 equivalents, per equivalent of compound (11). The reaction is generally conducted in an inert medium. With respect to the inert medium, there is no particular limitation as long as the medium is inert to the reaction system. Examples of inert media include dimethylformamide, dimethylacetamide, diethyl ether, tetrahydrofuran, methanol, ethanol and acetonitrile. The amount of the inert medium may be appropriately selected. For example, the inert medium is used in a volume amount which is 5 to 100 times (v/w) the weight amount of compound (11).

Generally, the reaction of compound (11) with an imide reagent is conducted under cooled or heated conditions, preferably under heated conditions. The completion of the reaction can be confirmed by observing the disappearance of the starting material. Generally, the reaction is completed within 3 hours to 2 days. It is preferred that the above-mentioned reaction be conducted in the presence of a basic compound. Examples of basic compounds include known organic basic compounds, such as triethylamine, pyridine and 4-methylmorpholine; and known inorganic basic compounds, such as potassium carbonate, sodium carbonate and sodium hydrogencarbonate. The basic compound can be used in an amount of from 1 to 100 equivalents per equivalent of compound (8); but preferably 1 to 5 equivalents, more preferably 1 to 1.5 equivalents, per equivalent of the imide reagent. The above-mentioned basic compound may also function as an inert medium.

The above-mentioned compound (11) can be obtained, for example, by reacting the above-mentioned compound (9) with a known amine compound which can be substituted with an amino-protecting group, such as ammonia (including aqueous ammonia or an ammonium salt which can generate ammonia under basic conditions), benzylamine, 4-methoxybenzylamine, 3,4-dimethoxybenzylamine, diphenylmethylamine or triphenylmethylamine. After reacting compound (9) with ammonia, the amino group of the resultant compound can be protected by treatment with the above-mentioned amino-protecting group, or the hydrogen atom of the amino group of the resultant compound can be replaced with a lower alkyl group by treatment with the above-mentioned alkylating reagent. The amine compound used in the reaction can be produced by a conventional method. Further, the amine compound is commercially available, and thus can be readily obtained and used. The amine compound is generally used in an amount of one equivalent or more, preferably 1 to 5 equivalents, per equivalent of compound (9).

The reaction of compound (9) with an amine compound is generally conducted in an inert medium. With respect to the inert medium, there is no particular limitation as long as the medium is inert to the reaction system. Examples of inert media include dimethylformamide, dimethylacetamide, diethyl ether, tetrahydrofuran, methanol, ethanol and acetonitrile. The amount of the inert medium may be appropriately selected. For example, the inert medium is used in a volume amount which is 5 to 100 times (v/w) the weight amount of compound (9).

Generally, the reaction is conducted under cooled or heated conditions, preferably under heated conditions. The completion of reaction can be confirmed by observing the disappearance of the starting material. Generally, the reaction is completed within 3 hours to 2 days. It is preferred that the reaction of compound (9) with an amine compound be conducted in the presence of a basic compound. Examples of basic compounds include known organic basic compounds, such as triethylamine, pyridine and 4-methylmorpholine; and known inorganic basic compounds, such as potassium carbonate, sodium carbonate and sodium hydrogencarbonate. The amount of the basic compound may be appropriately selected. For example, the basic compound is used in an amount of from 1 to 100 equivalents per equivalent of compound (9). The above-mentioned basic compound may also function as an inert medium. The above-mentioned amine compound can also be used in place of a basic compound or an inert medium.

In the present invention, compound (2) can be obtained in such manner as mentioned above.

In the present invention, leaving atom or group X in compound (3) which is one of the starting materials is an atom or group which can be eliminated from compound (3) during the reaction of compound (2) with compound (3) for producing compound (4). Generally, as the leaving atom or group, an atom or group having a high reactivity, such as a halogen atom (including a chlorine atom and a bromine atom), an organosulfonyloxy group (including a methanesulfonyloxy group and a p-toluenesulfonyloxy group) and a group constituting a symmetric acid anhydride, can be used. Further, a hydroxyl group can also be used as the leaving group. In this case, it is preferred that the hydroxyl group be used in combination with an acid activator mentioned below.

Compounds (3) used in the present invention are known compounds. Examples of compounds (3) include 1-naphthoyl chloride, 2-naphthoyl chloride, 1-naphthalenesulfonyl chloride, 2-naphthalenesulfonyl chloride, picolinoyl chloride hydrochloride, nicotinoylchloride hydrochloride, isonicotinoylchloride hydrochloride, 2-thenoyl chloride, 3-thenoyl chloride, 2-furoyl chloride, 3-furoyl chloride, 1-naphthalenecarboxylic acid, 2-naphthalenecarboxylic acid, picolinic acid, nicotinic acid, isonicotinic acid, 2-thiophenecarboxylic acid, 3-thiophenecarboxylic acid, 2-furancarboxylic acid and 3-furancarboxylic acid. Such compounds as mentioned above are commercially available, and sold by, for example, Tokyo Kasei Kogyo Co., Ltd., Japan and Aldrich Chemical Co., Inc., U.S.A. Therefore, these compounds can be readily obtained and used.

The reaction of compound (2) with compound (3) can be conducted by conventionally known amidation techniques. For example, when compound (3) has, as a leaving atom or group X, the above-mentioned atom or group having a high reactivity, the reaction of compound (2) with compound (3) is conducted in an inert medium. Examples of inert media include chloroform, methylene chloride, diethyl ether and tetrahydrofuran. With respect to the amount of each of compounds (2) and (3), compound (3) is generally used in an amount within the range of from 0.1 to 10 equivalents, preferably 1 to 2 equivalents per equivalent of compound (2). The amount of the inert medium may be appropriately selected. For example, the inert medium is used in a volume amount which is 5 to 100 times (v/w) the weight amount of compound (2). The reaction can be generally conducted at room temperature. The completion of reaction can be confirmed by observing the disappearance of the starting material. Generally, the reaction is completed within 1 hour to 3 days.

Further, it is preferred that the above-mentioned amidation reaction be conducted in the presence of a basic compound which may also function as an inert medium. Examples of basic compounds include known organic basic compounds, such as triethylamine, pyridine and 4-methylmorpholine; and known inorganic basic compounds, such as potassium carbonate, sodium carbonate and sodium hydrogencarbonate. The above-mentioned basic compound is used preferably in an equivalent amount to the amount of compound (3), or in slight excess relative to the amount of compound (3), for example, about 1.5 equivalents per equivalent of compound (3).

When compound (3) has a hydroxyl group as leaving group X, it is preferred that compound (3) be activated by a known acid activator before the reaction of compound (2) with compound (3). Examples of acid activators include isobutyl chloroformate, ethyl chloroformate, methyl chloroformate, dicyclohexylcarbodiimide (DCC), 1-ethyl-3-(3-dimethylaminopropyl)carbodiimide, N-hydroxysuccinimide and N-hydroxybenzotriazole.

For example, when a chloroformic ester, such as isobutyl chloroformate, ethyl chloroformate or methyl chloroformate, is used as an acid activator, compound (3), which is an acid, such as 3-thiophenecarboxylic acid or 3-furancarboxylic acid, can be activated by a reaction thereof with the chloroformic ester (such as isobutyl chloroformate, ethyl chloroformate or methyl chloroformate) in an inert medium in the presence of a basic compound. Examples of basic compounds include known organic basic compounds, such as triethylamine, pyridine and 4-methylmorpholine; and known inorganic basic compounds, such as potassium carbonate, sodium carbonate and sodium hydrogencarbonate. The above-mentioned basic compounds may also function as an inert medium.

The above-mentioned acid activator is used in an amount within the range of from 1 to 5 equivalents, preferably 1 to 1.5 equivalents, per equivalent of compound (3). The basic compound is used in an amount within the range of from 1 to 2 equivalents, preferably 1 to 1.5 equivalents, per equivalent of the acid activator used in the reaction. With respect to the inert medium, there is no particular limitation as long as the medium is inert to the reaction system of mentioned-above. The amount of the inert medium may be appropriately selected. However, the inert medium can generally be used in a volume amount which is 5 to 100 times (v/w) the weight amount of compound (3) used for the reaction. The reaction can be conducted at room temperature, however, preferably at a relatively low temperature of from about −25° C. to about 5° C. The completion of reaction can be confirmed by observing the disappearance of the starting material. Generally, the reaction is completed within 15 minutes to 2 hours to obtain a reaction mixture. The acid derivative of compound (3) activated by an acid activator may or need not be isolated from the reaction mixture before being used for a reaction with compound (2). Generally, however, the acid derivative of compound (3) is not isolated from the reaction mixture, but the obtained reaction mixture containing the acid derivative of compound (3) can be reacted in situ with compound (2).

As a result of the above-mentioned reaction of compound (2) with compound (3), compound (4) is obtained. When compound (4) has an amino-protecting group as $R^{11}$, the amino-protecting group must be eliminated.

As a method for the elimination of the amino-protecting group (deblocking), a known method can be employed, and an appropriate method is selected depending on the type of amino-protecting group. For example, when the amino-protecting group is tert-butoxycarbonyl group (Boc group) or the like, the deblocking is conducted by contacting a compound having an amino-protecting group with an acid, such as hydrochloric acid, sulfuric acid or trifluoroacetic acid. The acid for the deblocking is generally used in an amount of 1 equivalent or more, preferably from 1 to 100 equivalents per equivalent of compound (4). In this case, the acid may be appropriately diluted with a solvent. Examples of such solvents include chloroform, methylene chloride, diethyl ether, tetrahydrofuran, methanol and water. Generally, the reaction is conducted at a temperature of from −25° C. to 40° C., preferably around 0° C. The completion of reaction can be confirmed by observing the disappearance of the starting material. When it is observed by chromatography or the like that the desired compound is formed in a maximum amount, the reaction can be terminated. Generally, the reaction is completed within 1 hour to 24 hours.

When the amino-protecting group is a benzyloxycarbonyl group (Cbz group), a benzyl group or the like, the deblocking can be conducted by contacting a compound having an amino-protecting group with hydrogen gas in the presence of a catalyst, such as palladium black, activated carbon-palladium or platinum oxide. In this case, examples of solvents usable for the deblocking include diethyl ether, tetrahydrofuran, methanol, ethyl acetate, dimethylformamide and water. The amount of the solvent may be appropriately selected. However, the solvent can generally be used in a volume amount which is 5 to 100 times (v/w) the weight amount of compound (4) used for the reaction. The reaction can be conducted under cooled or heated conditions, however, preferably at room temperature. The completion of reaction can be confirmed by observing the disappearance of the starting material. When it is observed by chromatography or the like that the desired compound is formed in a maximum amount, the reaction can be terminated. Generally, the reaction is completed within 1 hour to 3 days.

Further, when the amino-protecting group is a benzyloxycarbonyl group (Cbz group) or the like, the deblocking can be conducted using a reagent, such as a solution of hydrobromic acid in acetic acid, trifluoroacetic acid, aluminum chloride, boron tribromide or the like. The reagent for the deblocking is usually used in an amount of 1 equivalent or more, preferably from 1 to 100 equivalents, per equivalent of compound (4). In this case, the acid may be appropriately diluted with a solvent. Examples of such solvents include chloroform, methylene chloride, diethyl ether and tetrahydrofuran.

Further, it is preferred that a scavenger, such as anisole and thioanisole, be present in the reaction system in order to capture benzyl cations formed during the reaction. The scavenger is generally used in an amount of 1 equivalent or more, preferably from 1 to 100 equivalents, per equivalent of compound (4). The reaction can be conducted under cooled or heated conditions, however, preferably at a temperature of from 0° C. to room temperature. The completion of reaction can be confirmed by observing the disappearance of the starting material. When it is observed by chromatography or the like that the desired compound is formed in a maximum amount, the reaction can be terminated. Generally, the reaction is completed within 1 hour to 3 days.

When the amino-protecting group is a 9-fluorenyloxycarbonyl group (Fmoc group), an ethoxycarbonyl group, a methoxycarbonyl group, an acetyl group or the like, the deblocking can be conducted using an organic basic compound (such as morpholine) or an inorganic basic compound (such as sodium hydroxide). The amount of the basic compound may be appropriately selected. For example, the basic compound is used in an amount of from 1 to 100 equivalents per equivalent of compound (4).

In the present invention, compound (1) having a hydrogen atom as $R^1$ can be obtained in such manner as mentioned above. Further, when it is intended to produce a compound (1) having a lower alkyl group as $R^1$ from the compound (1) having a hydrogen atom as $R^1$, it is possible to replace the hydrogen atom with a lower alkyl group using an alkylating reagent mentioned above, to thereby obtain compound (1)

having a lower alkyl group as $R^1$. These alkylating reagents may be used in an amount within the range of from 0.1 to 10 equivalents, preferably 1 to 5 equivalents, per equivalent of compound (1).

When the solvent used in the reaction for obtaining compound (1) is a hydrophobic organic solvent, compound (1) can be obtained by washing a reaction mixture with an alkaline aqueous solution or saturated saline to form an organic layer, separating the organic layer and then, concentrating the organic layer. When the solvent used in the reaction is a hydrophilic organic solvent, compound (1) can be obtained by subjecting a reaction mixture to distillation to thereby remove the solvent and obtain a residue, dissolving the residue in a hydrophobic organic solvent and then, treating the obtained solution in the same manner as mentioned above.

Generally, each of the above-mentioned intermediates obtained in respective steps of the procedure of synthesis of compound (1) is not isolated from the reaction mixture, but each of the obtained reaction mixtures containing respective intermediates can be used in the next step of the procedure in situ. If desired, each of these intermediates can be isolated and purified before being used in the next step of the reaction. The isolation and purification of intermediates and the purification of the final product, i.e. compound (1), can be conducted by appropriate combinations of known methods, such as column chromatography using silica gel or the like, recrystallization and extraction.

In the present invention, there is no particular limitation with respect to the pressure during each of the reactions. But generally, the reactions are conducted under atmospheric pressure.

For easy understanding of the steps of the above-mentioned two processes for producing compound (1) of the present invention, a flow chart illustrating the above-mentioned two processes is provided below.

Flow chart of the processes for the production of compound (1)

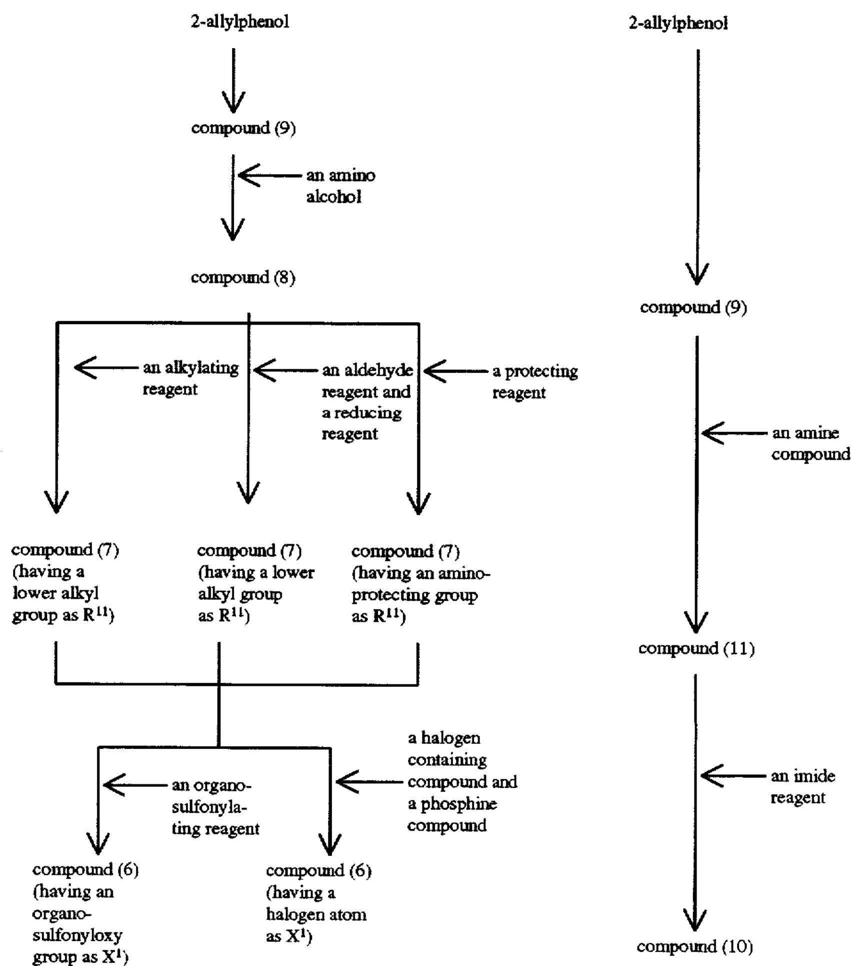

-continued

Flow chart of the processes for the production of compound (1)

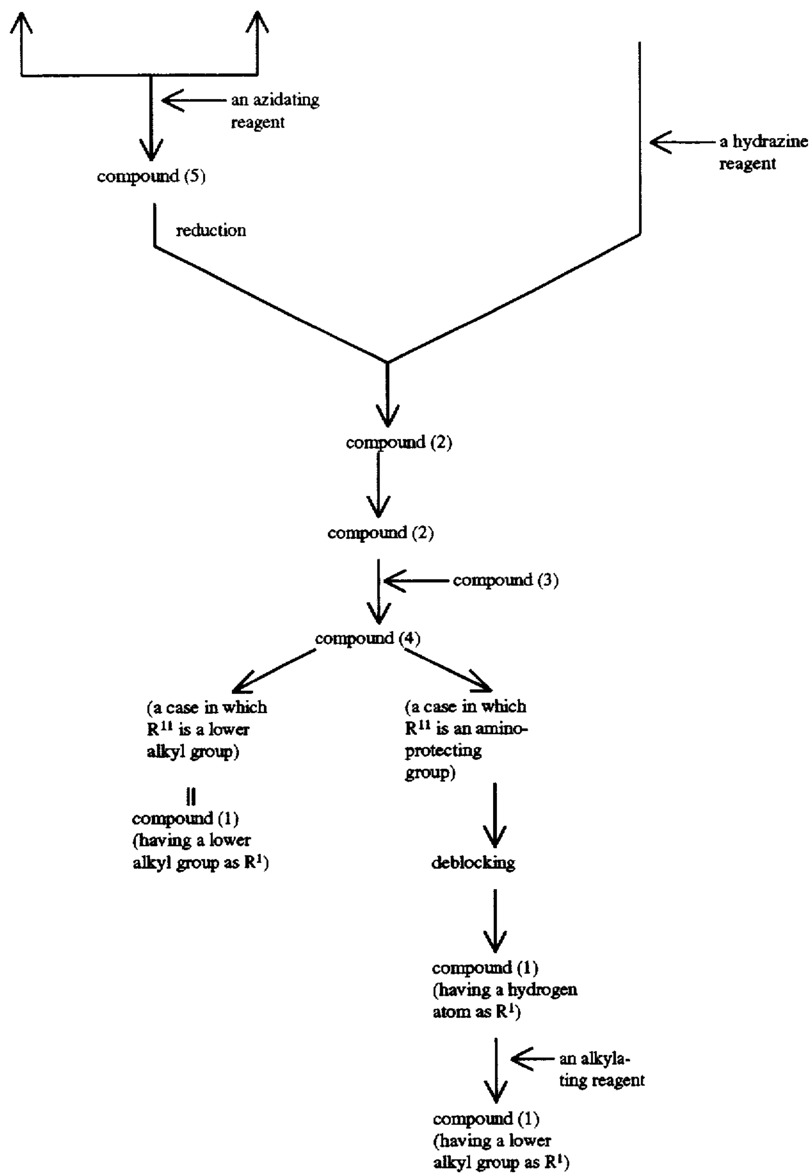

In the present invention, compound (1), which has an asymmetric carbon atom as shown in formula (1), may be in an optically active form or in the form of a racemic modification thereof.

Compound (1) which is in an optically active form can be isolated and collected by a conventional method. As examples of such a method, there can be mentioned a chromatographic resolution method using chiral stationary phase; and a method in which an enantiomeric salt of compound (1) is formed and then, the salt is subjected to optical resolution by selective crystallization or subjected to enzymatic hydrolysis using a stereoselective esterase, so that the desired compound in an optically active form can be obtained. Alternatively, the desired compound in optically active form can be obtained by using an optically active starting material.

Compound (1) of the present invention can be provided in the form of a pharmaceutically acceptable non-toxic salt thereof, if desired. Examples of such salts of compound (1) include salts thereof with inorganic acids, such as hydrochloric acid, sulfuric acid and phosphoric acid, and salts thereof with organic acids, such as acetic acid, propionic acid, tartaric acid, citric acid, glycolic acid, gluconic acid, succinic acid, malic acid, maleic acid, fumaric acid, mandelic acid, methanesulfonic acid, p-toluenesulfonic acid, aspartic acid and glutamic acid.

The above-mentioned non-toxic salts of compound (1) can be produced by a known method for producing a salt from a free base. For example, the hydrochloride of compound (1) of the present invention can be prepared by adding a solution of hydrochloric acid in methanol to compound (1) in an amount of 1 equivalent or more per equivalent of compound (1) to form the hydrochloride of compound (1) in the form of a precipitate, and then collecting the precipitate. When the hydrochloride of compound (1) is hardly deposited as a precipitate, an appropriate solvent (e.g., diethyl ether) can be added thereto to deposit the hydrochloride as a precipitate.

It was found that, when rats are intraperitoneally administered compound (1) or a non-toxic salt thereof of the present invention in an amount of 100 mg/kg, none of the rats die. Therefore, compound (1) or the non-toxic salt thereof is suitable as a drug. Compound (1) or a non-toxic salt thereof of the present invention has a high affinity for the 5-HT1A receptor and, therefore, can be advantageously used as an active ingredient of a pharmaceutical composition useful for treatment of a serotonergic neuron-related disease. In the present invention, a serotonergic neuron-related disease means a neuron-related disease which has correlations with serotonin. Specific examples of serotonergic neuron-related disease include anxiety, depression, eating disorder, high blood pressure, emesis (including emesis induced by motion sickness, space sickness, dizziness and drug, etc.), and the like.

For preparation of such a pharmaceutical composition, compound (1) or a non-toxic salt thereof can be combined with at least one pharmaceutically acceptable carrier, diluent or excipient and may be administered to a patient orally or parenterally by a conventional method.

The pharmaceutical composition of the present invention can be administered to a patient in the form of a solution for injection, intravenous drip, tablet, pill, powder, granule or capsule. For the preparation of such a pharmaceutical composition, various types of pharmaceutically acceptable carriers, diluents or excipients can be employed, depending on the form of the pharmaceutical composition.

For example, when compound (1) of the present invention is formulated into a medicine for oral administration (such as a tablet, granule, capsule or the like), there can be employed excipients, such as starch, lactose, refined sugar, mannitol, carboxymethyl cellulose, corn starch and inorganic salts; disintegrating reagents, such as methylcellulose, sodium salt of carboxymethyl cellulose, hydroxypropyl cellulose, crystalline cellulose, ethylcellulose, polyvinyl pyrrolidone and macrogol; surfactants, such as sodium laurylsulfate, soybean lecithin, sucrose esters of fatty acids and polysorbate 80; lubricants, such as talc, wax, hydrated vegetable oils, sucrose esters of fatty acids, magnesium stearate and calcium stearate; fluidity promoting reagent; sweetening and flavoring reagents; and the like. The pharmaceutical composition of the present invention can be administered in the form of an emulsion, syrup or elixir.

When compound (1) of the present invention is formulated into a medicine for parenteral administration, a diluent, such as distilled water for injection, physiological saline, an aqueous solution of glucose, a vegetable oil for injection, propylene glycol or polyethylene glycol, can be used. In addition, if desired, other additives, such as a germicide, antiseptic, stabilizer, isotonic reagent and soothing reagent, can be used.

A pharmaceutical composition of the present invention for treating a serotonergic neuron-related disease may be administered to a patient orally or parenterally. When the pharmaceutical composition is parenterally administered, it can be administered by way of intramuscular injection or intravenous injection, and it can also be administered endermically, transnasally or transvaginally.

The dose of the pharmaceutical composition of the present invention for treating a serotonergic neuron-related disease varies depending on various-factors, such as the manner of administration, age, weight, condition of the patient, etc. However, the dose may generally be about 0.001 to about 100 mg/kg per day for an adult in terms of the amount of compound (1).

In order to demonstrate the pharmacological activities of compound (1) and a salt thereof of the present invention, tests were conducted with respect to compounds (1) synthesized in the Examples described below. The procedures and results of the tests are as follows.

1. Affinity for serotonin (5-HT) 1A receptor (1) Method (A) Preparation of rat hippocampal membrane fraction A male SD strain rat (7-week old; Charles River) was decapitated, and brain was taken out therefrom quickly. 50 mM Tris-HCl buffer (pH 7.4) was added to the brain under ice cooling to obtain a suspension. The resultant suspension was homogenized, and then subjected to centrifugation at 48,000 g for 15 minutes, to thereby obtain a precipitate. The precipitate was resuspended in the same Tris-HCl buffer as used above. The resultant suspension was incubated at 30° C. for 20 minutes to decompose endogenous serotonin of the rat hippocampal membrane, followed by centrifugation at 48,000 g for 15 minutes to thereby obtain a precipitate. The resultant precipitate was used as a rat hippocampal membrane fraction in the following procedures.

(B) Method for the evaluation of the binding ability of $^{3}$H-8-hydroxy-2-dipropylaminotetralin ($^{3}$H-8-OH-DPAT) to serotonin 1A receptor The rat hippocampal membrane fraction prepared in step (A) above (about 0.1 to 0.2 mg in terms of proteins) was reacted with 0.5 nM (final concentration) $^{3}$H-8-OH-DPAT (which is commercially available from DuPont-NEN Research Products, U.S.A.) and 0.01 mM (final concentration) pargyline (which is commercially available from Sigma Chemical Company, U.S.A.) at 30° C. for 30 minutes to effect a reaction. The resultant reaction mixture was subjected to suction filtration using a Whatman GF/C filter, to thereby terminate the reaction. The radioactivity of $^{3}$H-8-OH-DPAT adsorbed on the filter was determined using a liquid scintillation counter. The obtained value is regarded as a total amount (TB) of specifically binding 3H-8-OH-DPAT and non-specifically binding $^{3}$H-8-OH-DPAT. On the other hand, substantially the same procedure as mentioned above was repeated, except that 0.01 mM (final concentration) serotonin was added to the $^{3}$H-8-OH-DPAT and pargyline. The radioactivity of $^{3}$H-8-OH-DPAT adsorbed on the filter was determined in the same manner as mentioned above. The obtained value is regarded as the amount (NB) of non-specifically binding $^{3}$H-8-OH-DPAT.

Further, substantially the same procedure as mentioned above was repeated, except that, instead of serotonin, a test compound was used in a predetermined concentration. The radioactivity of $^{3}$H-8-OH-DPAT adsorbed on the filter was determined in the same manner as mentioned above. The obtained value is regarded as the amount (DTB) of binding $^{3}$H-8-OH-DPAT.

(C) Calculation of Ki value

The inhibition ratio of the test compound (at a certain concentration) against the binding of $^{3}$H-8-OH-DPAT (the inhibition ratio is hereinafter referred to simply as "binding inhibition ratio") was calculated according to the following formula:

$$\text{Binding inhibition ratio (\%)} = 100 - [(DTB - NB) \div (TB - NB)] \times 100$$

With respect to each of the test compounds, the binding inhibition ratios at various concentrations (from a higher concentration to a lower concentration) were determined. The binding inhibition ratios were plotted, taking the logarithmic value of the concentration of test compound as the abscissa value.; and the binding inhibition ratio as the ordinate value. Then, a curve was drawn by the non-linear least square method. From the curve thus drawn, the $IC_{50}$ value (the concentration at which a test compound inhibits the binding of $^3$H-8-OH-DPAT to the serotonin 1A receptor by 50%) was determined with respect to each of the test compounds.

The Ki value was determined according to the following formula:

$$Ki=IC_{50}+[1+(L)/Kd]$$

wherein:

(L) is the concentration (0.2 nM) of a radioactive ligand ($^3$H-8-OH-DPAT) used in the test;

Kd is the concentration (0.7174 nM) at which the radioactive ligand ($^3$H-8-OH-DPAT) exhibits the affinity for the serotonin 1A receptor; and $IC_{50}$ is the concentration of a test compound at which the test compound inhibits the binding of the radioactive ligand ($^3$H-8-OH-DPAT) to the serotonin 1A receptor by 50%.

(2) Results

The results of the measurement of the binding ability of compounds (1) of the present invention to the serotonin 1A receptor are shown in Table 1below. Each of the compounds (1) used in the above tests was tested in the form of a hydrochloride salt thereof, and represented in Table 1 by the compound number used in Examples described below.

TABLE 1

| Compound No. | 5-HT1A Ki (nM) |
|---|---|
| 101B | 6.0 |
| 102B | 5.0 |
| 103B | 40 |
| 105B | 12 |
| 106B | 1.9 |
| 107B | 2.3 |
| 108B | 21 |
| 112A | 1.7 |
| 113A | 8.5 |
| 114B | 2.7 |
| 115B | 4.9 |

2. Affinity for adrenaline α1 receptor (1) Method (A) Preparation of membrane fraction of rat adrenaline α1 receptor A male SD strain rat (7-week old; Charles River) was decapitated, and brain was taken out therefrom quickly. Cerebral cortex of the rat was separated and extracted at 50 mM under ice cooling. The extracted cerebral cortex was frozen at −80° C. for 24 hours or longer. This frozen system was gradually thawed under ice cooling and then, 50 mM Tris-HCl buffer (pH 7.4) was added to the brain under ice cooling to obtain a suspension. The resultant suspension was homogenized, and then subjected to centrifugation at 48,000 g for 15 minutes, to thereby obtain a precipitate. The precipitate thus obtained was washed twice and resuspended in the same Tris-HCl buffer as used above. The resultant precipitate was used as a membrane fraction of rat adrenaline α1 receptor in the following procedures.

(B) Method for the evaluation of the binding ability of $^3$H-Prazosin to rat adrenaline α1 receptor The membrane fraction of rat adrenaline α1 receptor prepared in step (A) above was reacted with 0.2 nM (final concentration) 3H-Prazosin (which is commercially available from DuPont-NEN Research Products) and 0.005% (final concentration) ascorbic acid at 25° C. for 30 minutes to effect a reaction. The total volume amount of the reaction mixture was 1 ml. The resultant reaction mixture was subjected to suction filtration using a Whatman GF/C filter, and the filter was washed three times in 50 mM Tris-HCl buffer (pH 7.4, 4 ml), transferred to a vial and then, the radioactivity of Prazosin absorbed on the filter was determined using a liquid scintillation counter. The obtained value is regarded as a total amount (TB) of specifically binding $^3$H-Prazosin and non-specifically binding $^3$H-Prazosin. On the other hand, substantially the same procedure as mentioned above was repeated, except that 100 nM (final concentration) Prazosin was added to the $^3$H-Prazosin and ascorbic acid. The radioactivity of $^3$H-Prazosin adsorbed on the filter was determined in the same manner as mentioned above. The obtained value is regarded as the amount (NB) of non-specifically binding $^3$H-Prazosin.

Further, substantially the same procedure as mentioned above was repeated, except that, instead of Prazosin, a test compound was used in a predetermined concentration. The radioactivity of $^3$H-Prazosin adsorbed on the filter was determined in the same manner as mentioned above. The obtained value is regarded as the amount (DTB) of binding $^3$H-Prazosin.

(C) Calculation of Ki value

The inhibition ratio of the test compound (at a certain concentration) against the binding of $^3$H-Prazosin was calculated according to the following formula:

$$\text{Binding inhibition ratio } (\%)=100-[(DTB-NB)+(TB-NB)]\times 100$$

With respect to each of the test compounds, the binding inhibition ratios at various concentrations (from a higher concentration to a lower concentration) were determined. The binding inhibition ratios were plotted, taking the logarithmic value of the concentration of the test compound as the abscissa value, and the binding inhibition ratio as the ordinate value. Then, a curve was drawn by the non-linear least square method. From the curve thus drawn, the $IC_{50}$ value (the concentration at which a test compound inhibits the binding of $^3$H-Prazosin to the adrenaline α1 receptor by 50%) was determined with respect to each of the test compounds.

The Ki value was determined according to the following formula:

$$Ki=IC_{50}+[1+(L)/Kd]$$

wherein:

(L) is the concentration (0.2 nM) of a radioactive ligand ($^3$H-Prazosin) used in the test; Kd is the concentration (0.133 nM) at which the radioactive ligand ($^3$H-Prazosin) exhibits the affinity for the adrenaline α1 receptor; and $IC_{50}$ is the concentration of a test compound at which the test compound inhibits the binding of the radioactive ligand ($^3$H-Prazosin) to the adrenaline α1 receptor by 50%.

(2) Results

The results of the measurement of the binding affinity of compounds (1) of the present invention to the adrenaline α1 receptor are shown in Table 2 below. Each of the compounds (1) used in the above tests was tested in the form of a hydrochloride salt thereof, and represented in Table 2 by the compound number used in Examples described below.

TABLE 2

| Compound No. | Adrenaline α1 Ki (nM) |
|---|---|
| 101B | 150 |
| 102B | 140 |
| 106B | 240 |
| 107B | 230 |
| 111A | 160 |
| 112B | 320 |
| 113B | 95 |
| 114B | 96 |
| 116A | 530 |
| 117A | 580 |

From the above results, it has been confirmed that compounds (1) of the present invention have a strong affinity for a serotonin 1A receptor while exhibiting a weak affinity for an adrenaline α1 receptor, thus exhibiting selective activities. Therefore, it will be understood that compounds (1) of the present invention are useful for prevention and treatment of serotonergic neuron-related diseases, such as anxiety, depression, eating disorder, high blood pressure, emesis (including emesis induced by motion sickness, space sickness, dizziness, drug, etc.) and the like.

3. Activities against emesis (1) Method

The activities of individual compounds against emesis were examined using Suncus murinus. Suncus murinus is a small animal belonging to the Soricidae family. It has been known that suncus is likely to suffer from motion sickness and is susceptible to occurrence of emesis [see "Seitai-no-kagaku (Science of living body)", 42, 538 (1990)]. Suncus is likely to show symptoms like the symptoms of human motion sickness under the stimulus of simple acceleration, finally leading to the occurrence of emesis. It has been known that a drug, such as cisplatin, has an emesis-inducing activity.

In this test, test compounds were individually administered intraperitoneally to suncus. 30 minutes after the administration, acceleration-stimulus (amplitude: 4 cm; frequency; 1 Hz) was given to the suncus, and the suncus thus treated was observed as to whether emesis occurred or not.

(2) Results

The results of the evaluation of antiemetic activity of compounds (1) of the present invention are shown in Table 3 below. Each of the compounds (1) used in the above tests was tested in the form of a hydrochloride salt thereof, and represented in Table 3 by the compound number used in Examples described below.

TABLE 3

| Sample | Dose (mg/kg) | Time for occurrence of emesis (min. sec) | Number of tested suncus |
|---|---|---|---|
| Physiological saline | | 0.55 | 4 |
| 106B | 1 | 8.50 | 4 |
| 108B | 1 | 4.56 | 4 |
| 112B | 3 | 6.03 | 4 |
| 113B | 1 | 7.44 | 4 |
| 114B | 1 | 3.50 | 4 |
| 115B | 1 | 5.56 | 4 |

From the results, it has been confirmed that compounds (1) of the present invention very effectively suppress emesis. Therefore, it is concluded that compounds (1) and non-toxic salts thereof of the present invention are useful for preventing and treating space sickness, dizziness, drug-induced emesis and the like.

BEST MODE FOR CARRYING OUT THE INVENTION

The present invention will be described in greater detail with reference to the following Reference Examples and Examples, which, however, should not be construed to be limiting the scope of the present invention.

Physical properties (i.e., NMR spectra and mass spectra) of the compounds obtained in the Reference Examples and Examples (which compounds are represented by the numbers) are shown in Table 4 below.

Reference Example 1

Synthesis of 2-[N-(4-aminobutyl)-N-(tert-butoxycarbonyl)]aminomethyl-2,3-dihydrobenzo[b]furan (compound 001H)

Step A Synthesis of 2-acetoxyallylbenzene (compound 001A)

1.3 ml (10 mmol) of 2-allylphenol was dissolved in 6.5 ml of pyridine, followed by cooling to 0° C. To the resultant solution were added 24 mg (0.2 mmol) of dimethylaminopyridine and 1.9 ml (20 mmol) of acetyl chloride. The resultant mixture was stirred at 0° C. for 2 hours to effect a reaction. To the resultant reaction mixture was added 50 ml of chloroform to obtain a mixture. The obtained mixture was successively washed with 50 ml of a saturated aqueous sodium hydrogencarbonate solution, 50 ml of water and 50 ml of saturated saline, to thereby form a chloroform layer containing the desired compound 001A, followed by separation of the chloroform layer. The chloroform layer thus separated was dehydrated by means of a Whatman 1PS filter paper and then, concentrated in vacuo. The obtained residue was subjected to distillation in vacuo (78° to 80° C./4 mmHg) to thereby obtain 1.64 g of compound 001A as a transparent oily substance (yield: 93%).

Step B Synthesis of 3-(2-acetoxyphenyl)-1,2-dibromopropane (compound 001B)

580 mg (3.0 mmol) of compound 001A, which had been prepared in Step A, was dissolved in 5 ml of carbon tetrachloride, followed by cooling to 0° C. To the resultant solution was dropwise added 0.16 ml (3.0 mmol) of bromine and then, the resultant mixture was stirred at 0° C. for 2 hours to effect a reaction. To the resultant reaction mixture was added 20 ml of chloroform to obtain a mixture. The obtained mixture was successively washed with 20 ml of an aqueous sodium hydrogensulfite solution, 20 ml of water and 20 ml of saturated saline, to thereby form a chloroform layer containing the desired compound 001B, followed by separation of the chloroform layer. The chloroform layer thus separated was dehydrated by means of a Whatman 1PS filter paper and then, concentrated in vacuo to thereby obtain 0.93 g of compound 001B as a transparent oily substance (yield: 92%).

Step C Synthesis of 2-bromomethyl-2,3-dihydrobenzo[b]furan (compound 001C)

340 mg (1.0 mmol) of compound 001B, which had been prepared in Step B, was dissolved in 3 ml of ethanol, followed by cooling to 0° C. To the resultant solution was dropwise added 1.2 ml (1.2 mmol) of a 1N solution of sodium ethoxide in ethanol and then, the resultant mixture was stirred at 0° C. for 2 hours to effect a reaction. To the resultant reaction mixture was added 20 ml of chloroform to obtain a mixture. The obtained mixture was successively washed with 20 ml of a 10% aqueous citric acid solution, 20 ml of water and 20 ml of saturated saline, to thereby form a chloroform layer containing the desired compound 001C, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (30:1), to thereby obtain 140 mg of compound 001C as a transparent oily substance (yield: 66%).

Step D Synthesis of 2-[N-(4-hydroxybutyl)]aminomethyl-2,3-dihydrobenzo[b]furan (compound 001D)

430 mg (2.0 mmol) of compound 001C, which had been prepared in Step C, was dissolved in 4 ml of acetonitrile. To the resultant solution were added 0.92 ml (10.0 mmol) of 4-amino-1-buthanol and 550 mg (4.0 mmol) of potassium carbonate and then, the resultant mixture was stirred at 80° C. for 8 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 001D, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol-concentrated aqueous ammonia (10:1:0.1), to thereby obtain 300 mg of compound 001D as a light yellow oily substance (yield: 67 %).

Step E Synthesis of 2-[N-(tert-butoxycarbonyl)-N-(4-hydroxybutyl)]aminomethyl-2,3-dihydrobenzo[b]furan (compound 001E)

220 mg (1.0 mmol) of compound 001D, which had been prepared in Step D, was dissolved in 2 ml of methylene chloride, followed by cooling to 0° C. To the resultant solution were added 0.15 ml (1.1 mmol) of triethylamine and 240 mg (1.1 mmol) of a ditertiary butyl dicarbonate. The resultant mixture was stirred at room temperature for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 001E, followed by separation of the chloroform layer. The chloroform layer thus separated was dehydrated by means of a Whatman 1PS filter paper and then, concentrated in vacuo. The obtained residue was purified by silica gel column chromatography. That is, the residue was applied to a column of 10 g of silica gel (Art. 9385, manufactured and sold by E. Merck, Darmstadt, Germany) and eluted with chloroform to thereby obtain 306 mg of compound 001E as a transparent oily substance (yield: 95%).

Step F Synthesis of 2-{N-(tert-butoxycarbonyl)-N-[4-(p-toluenesulfonyloxy)butyl]}aminomethyl-2,3-dihydrobenzo[b]furan (compound 001F)

322 mg (1.00 mmol) of compound 001E, which had been prepared in Step E, was dissolved in 4 ml of methylene chloride, followed by cooling to 0° C. To the resultant solution were added 0.56 ml (4.0 mmol) of triethylamine and 300 mg (1.58 mmol) of p-toluenesulfonyl chloride. The resultant mixture was stirred at room temperature for 24 hours to effect a reaction. To the resultant reaction mixture was added 50 ml of chloroform to obtain a mixture. The obtained mixture was successively washed with 50 ml of water and 50 ml of saturated saline, to thereby form a chloroform layer containing the desired compound 001F, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with hexane-ethyl acetate (5:1), to thereby obtain 459 mg of compound 001F as a transparent oily substance (yield: 96%).

Step G Synthesis of 2-[N-(4-azidobutyl)-N-(tertbutoxycarbonyl)]aminomethyl-2,3-dihydrobenzo[b]furan (compound 001G)

184 mg (0.39 mmol) of compound 001F, which had been prepared in Step F, was dissolved in 1 ml N,N-dimethylformamide. To the resultant solution was added 100 mg (1.54 mmol) of sodium azide and then, the resultant mixture was stirred at 40° C. for 4 hours to effect a reaction. To the resultant reaction mixture was added 20 ml of chloroform to obtain a mixture. The obtained mixture was successively washed with 20 ml of water and 20 ml of saturated saline, to thereby form a chloroform layer containing the desired compound 00G, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with hexane-ethyl acetate(20:1), to thereby obtain 120 mg of compound 001G as a transparent oily substance (yield: 89%).

Step H Synthesis of 2-[N-(4-aminobutyl)-N-(tertbutoxycarbonyl)]aminomethyl-2,3-dihydrobenzo[b]furan (compound 001H)

117 mg (0.34 mmol) of compound 001G, which had been prepared in Step G, was dissolved in 2 ml of methanol. To the resultant solution was added 15 mg of 10% activated carbon-palladium and then, the resultant mixture was stirred at room temperature for 24 hours under the atmosphere of hydrogen to effect a reaction. The resultant reaction mixture was subjected to filtration through a Celite filter to filter off insoluble substances, which were then washed with a small amount of methanol, to thereby obtain a filtrate. The solvent of the filtrate was concentrated in vacuo to thereby obtain 108 mg of compound 001H as a transparent oily substance (yield: 100%). Compound 001H obtained in the above-mentioned manner was used for the subsequent reactions for producing compounds which are mentioned in Examples below without being further purified.

Reference Example 2

Synthesis of 2-[N-(2-aminoethyl)-N-benzyl] aminomethyl- 2,3-dihydrobenzo[b]furan (compound 002C)

Step A Synthesis of 2-(N-benzyl)aminomethyl-2,3-dihydrobenzo[b]furan (compound 002A)

1.07 g (5.0 mmol) of compound 001C, which had been prepared in Step C of Reference Example 1, was dissolved in 11 ml of acetonitrile. To the resultant solution were added 1.64 ml (15.0 mmol) of benzylamine and 2.07 g (15.0 mmol) of potassium carbonate. The resultant mixture was stirred at 80° C. for 8 hours to effect a reaction. To the resultant reaction mixture was added 100 ml of chloroform to obtain a mixture. The obtained mixture was successively washed with 100 ml of water and 100 ml of saturated saline, to thereby form a chloroform layer containing the desired compound 002A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 50 g of silica gel (Art. 9385, manufactured and sold by E. Merck, Darmstadt, Germany) and eluted with chloroform, to thereby obtain 873 mg of compound 002A as a yellow oily substance (yield: 73%).

Step B Synthesis of 2-[N-benzyl-N-(2-phthalimidoethyl) ]aminomethyl-2,3-dihydrobenzo[b]furan (compound 002B)

2.39 g (10.0 mmol) of compound 002A, which had been prepared in Step A, was dissolved in 24 ml of acetonitrile. To the resultant solution were added 5.08 g (20.0 mmol) of N-(2-bromoethyl)phthalimide and 2.76 g (20.0 mmol) of potassium carbonate and then, the resultant mixture was stirred at 80° C. for 8 hours to effect a reaction. To the resultant reaction mixture was added 100 ml of chloroform to obtain a mixture. The obtained mixture was successively washed with 100 ml of water and 100 ml of saturated saline, to thereby form a chloroform layer containing the desired compound 002B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 50 g of silica gel (Art. 9385, manufactured and sold by E. Merck, Darmstadt, Germany) and eluted with a mixed solvent of hexane-ethyl acetate (20:1), to thereby obtain 3.08 g of compound 002B as a yellow oily substance (yield: 75%).

Step C Synthesis of 2-[N-(2-aminoethyl)-N-benzyl] aminomethyl-2,3-dihydrobenzo[b]furan (compound 002C)

2.06 g (5.00 mmol) of compound 002B, which had been prepared in Step B, was dissolved in 20 ml of a mixed solvent of methylene chloride-ethanol (9:1). To the resultant solution was added 0.29 ml (6.00 mmol) of a 100% hydrazine hydrate at 0° C. and then, the resultant mixture was stirred at room temperature for 3 days to effect a reaction. To the resultant reaction mixture was added 50 ml of chloroform to obtain a mixture. The obtained mixture was successively washed with 50 ml of water and 50 ml of saturated saline, to thereby form a chloroform layer containing the desired compound 002C, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 50 g of silica gel (Art. 9385, manufactured and sold by E. Merck, Darmstadt, Germany) and eluted with a mixed solvent of chloroform-methanol-concentrated aqueous ammonia (30:1:0.1), to thereby obtain 1.19 g of compound 002C as a yellow oily substance (yield: 84%).

Reference Example 3

Synthesis of 2-[N-(3-aminopropyl)-N-benzyl] aminomethyl-2,3-dihydrobenzo[b]furan (compound 003B)

Step A Synthesis of 2-[N-benzyl-N-(3-phthalimidopropyl)]aminomethyl-2,3-dihydrobenzo[b] furan (compound 003A)

864 mg (3.60 mmol) of compound 002A, which had been prepared in Step A of Reference Example 2, was dissolved in 9 ml of acetonitrile. To the resultant solution were added 1.94 g (7.20 mmol) of N-(3-bromopropyl)phthalimide and 1.11 g (8.00 mmol) of potassium carbonate. The resultant mixture was stirred at 80° C. for 8 hours to effect a reaction. To the resultant reaction mixture was added 20 ml of chloroform to obtain a mixture. The obtained mixture was successively washed with 20 ml of water and 20 ml of saturated saline, to thereby form a chloroform layer containing the desired compound 003A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 20 g of silica gel (Art. 9385, manufactured and sold by E. Merck, Darmstadt, Germany) and eluted with a mixed solvent of hexane-ethyl acetate (10:1), to thereby obtain 1.47 g of compound 003A as a yellow oily substance (yield: 98%).

Step B Synthesis of 2-[N-(3-aminopropyl)-N-benzyl] aminomethyl-2,3-dihydrobenzo[b]furan (compound 003B)

1.28 g (3.00 mmol) of compound 003A, which had been prepared in Step A, was dissolved in 20 ml of a mixed solvent of methylene chloride-ethanol (9:1). To the resultant solution was added 0.17 ml (3.60 mmol) of a 100% hydrazine hydrate at 0° C. and then, the resultant mixture was stirred at room temperature for 2 days to effect a reaction. To the resultant reaction mixture was added 50 ml of chloroform to obtain a mixture. The obtained mixture was successively washed with 50 ml of water and 50 ml of saturated saline, to thereby form a chloroform layer containing the desired compound 003B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 20 g of silica gel (Art. 9385, manufactured and sold by E. Merck, Darmstadt, Germany) and eluted with a mixed solvent of chloroform-methanol-concentrated aqueous ammonia (30:1:0.1), to thereby obtain 678 mg of compound 003B as a yellow oily substance (yield: 76%).

EXAMPLE 1

Synthesis of 2-{N-[4-(1-naphthoylamino)butyl]} aminomethyl-2,3-dihydrobenzo[b]furan (compound 101B)

Step A Synthesis of 2-{N-(tert-butoxycarbonyl)-N-[4-(1-naphthoylamino)butyl]}aminomethyl-2,3-dihydrobenzo[b] furan (compound 101A)

160 mg (0.50 mmol) of compound 001H, which had been prepared in Step H of Reference Example 1, was dissolved in 2.0 ml of methylene chloride, followed by cooling to 0° C. To the resultant solution were added 0.14 ml (1.0 mmol) of triethylamine and 0.09 ml (0.6 mmol) of 1-naphthoyl chloride. The resultant mixture was gradually heated from 0° C. and stirred at room temperature for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 101A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (200:1), to thereby obtain 236 mg of compound 101A as a transparent oily substance (yield: 100%).

Step B Synthesis of 2-{N-[4-(1-naphthoylamino)butyl]}aminomethyl-2,3-dihydrobenzo[b]furan (compound 101B)

226 mg (0.48 mmol) of compound 101A, which had been prepared in Step A, was cooled to 0° C. To the cooled compound was added 0.37 ml of trifluoroacetic acid and then, the resultant mixture was stirred at 0° C. for 2 hours to effect a reaction. The resultant reaction mixture was concentrated in vacuo to thereby obtain a residue, which was then dissolved in 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 101B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (25:1), to thereby obtain 141 mg of compound 101B as a light yellow oily substance (yield: 79%).

EXAMPLE 2

Synthesis of 2-{N-[4-(2-naphthoylamino)butyl]}aminomethyl-2,3-dihydrobenzo[b]furan (compound 102B)

Step A Synthesis of 2-{N-(tert-butoxycarbonyl)-N-[4-(2-naphthoylamino)butyl]}aminomethyl-2,3-dihydrobenzo[b]furan (compound 102A)

160 mg (0.50 mmol) of compound 001H, which had been prepared in Step H of Reference Example 1, was dissolved in 2.0 ml of methylene chloride, followed by cooling to 0° C. To the resultant solution were added 0.14 ml (1.0 mmol) of triethylamine and 114 mg (0.60 mmol) of 2-naphthoyl chloride. The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 102A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (200:1), to thereby obtain 224 mg of compound 102A as a light yellow oily substance (yield: 95%).

Step B Synthesis of 2-{N-[4-(2-naphthoylamino)butyl]}aminomethyl-2,3-dihydrobenzo[b]furan (compound 102B)

220 mg (0.46 mmol) of compound 102A, which had been prepared in Step A, was cooled to 0° C. To the cooled compound was added 0.35 ml of trifluoroacetic acid and then, the resultant mixture was stirred at 0° C. for 2 hours to effect a reaction. The resultant reaction mixture was concentrated in vacuo to thereby obtain a residue, which was then dissolved in 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 102B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (20:1), to thereby obtain 141 mg of compound 102B as a light yellow oily substance (yield: 82%).

EXAMPLE 3

Synthesis of 2-{N-[4-(4-pyridylcarbonylamino)butyl]}aminomethyl-2,3-dihydrobenzo[b]furan (compound 103B)

Step A Synthesis of 2-{N-(tert-butoxycarbonyl)-N-[4-(4-pyridylcarbonylamino)butyl]}aminomethyl-2,3-dihydrobenzo[b]furan (compound 103A)

160 mg (0.50 mmol) of compound 001H, which had been prepared in Step H of Reference Example 1, was dissolved in 2.0 ml of methylene chloride, followed by cooling to 0° C. To the resultant solution were added 0.28 ml (2.0 mmol) of triethylamine and 107 mg (0.60 mmol) of isonicotinoyl chloride hydrochloride (manufactured and sold by Tokyo Kasei Kogyo Co., Ltd., Japan). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 103A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (100:1), to thereby obtain 198 mg of compound 103A as a transparent oily substance (yield: 93%).

Step B Synthesis of 2-{N-[4-(4-pyridylcarbonylamino)butyl]}aminomethyl-2,3-dihydrobenzo[b]furan (compound 103B)

194 mg (0.46 mmol) of compound 103A, which had been prepared in Step A, was cooled to 0° C. To the cooled compound was added 0.35 ml of trifluoroacetic acid and then, the resultant mixture was stirred at 0° C. for 2 hours to effect a reaction. The resultant reaction mixture was concentrated in vacuo to thereby obtain a residue, which was then dissolved in 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 103B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (20:1), to thereby obtain 129 mg of compound 103B as a light yellow oily substance (yield: 87%).

EXAMPLE 4

Synthesis of 2-{N-[4-(3-pyridylcarbonylamino) butyl]}aminomethyl-2,3-dihydrobenzo[b]furan (compound 104B)

Step A Synthesis of 2-{N-(tert-butoxycarbonyl)-N-[4-(3-pyridylcarbonylamino)butyl]}aminomethyl-2,3-dihydrobenzo[b]furan (compound 104A)

160 mg (0.50 mmol) of compound 001H, which had been prepared in Step H of Reference Example 1, was dissolved in 1.6 ml of methylene chloride, followed by cooling to 0° C. To the resultant solution were added 0.21 ml (1.5 mmol) of triethylamine and 107 mg (0.6 mmol) of nicotinoyl chloride hydrochloride (manufactured and sold by Tokyo Kasei Kogyo Co., Ltd., Japan). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 104A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (50:1), to thereby obtain 200 mg of compound 104A as a light yellow oily substance (yield: 94%).

Step B Synthesis of 2-{N-[4-(3-pyridylcarbonylamino) butyl]}aminomethyl-2,3-dihydrobenzo[b]furan (compound 104B)

187 mg (0.44 mmol) of compound 104A, which had been prepared in Step A, was cooled to 0° C. To the cooled compound was added 2.0 ml of trifluoroacetic acid and then, the resultant mixture was stirred at 0° C. for 1.5 hours to effect a reaction. The resultant reaction mixture was concentrated in vacuo to thereby obtain a residue, which was then dissolved in 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 104B, followed by separation of the chloroform layer. The chloroform layer thus separated was dehydrated by means of a Whatman 1PS filter paper and then, concentrated in vacuo to thereby obtain 139 mg of compound 104B as a light yellow oily substance (yield: 97%).

EXAMPLE 5

Synthesis of 2-{N-[4-(2-pyridylcarbonylamino) butyl]}aminomethyl-2,3-dihydrobenzo[b]furan (compound 105B)

Step A Synthesis of 2-{N-(tert-butoxycarbonyl)-N-[4-(2-pyridylcarbonylamino)butyl]}aminomethyl-2,3-dihydrobenzo[b]furan (compound 105A)

160 mg (0.50 mmol) of compound 001H, which had been prepared in Step H of Reference Example 1, was dissolved in 1.6 ml of methylene chloride, followed by cooling to 0° C. To the resultant solution were added 0.21 ml (1.5 mmol) of triethylamine and 107 mg (0.6 mmol) of picolinoyl chloride hydrochloride (manufactured and sold by Tokyo Kasei Kogyo Co., Ltd., Japan). The resultant mixture was stirred at 0° C. for 1.5 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline to thereby form a chloroform layer containing the desired compound 105A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 175 mg of compound 105A as a transparent oily substance (yield: 74%).

Step B Synthesis of 2-{N-[4-(2-pyridylcarbonylamino) butyl]}aminomethyl-2,3-dihydrobenzo[b]furan (compound 105B)

170 mg (0.37 mmol) of compound 105A, which had been prepared in Step A, was cooled to 0° C. To the cooled compound was added 2.0 ml of trifluoroacetic acid and then, the resultant mixture was stirred at 0° C. for 1.5 hours to effect a reaction. The resultant reaction mixture was concentrated in vacuo to thereby obtain a residue, which was then dissolved in 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 105B, followed by separation of the chloroform layer. The chloroform layer thus separated was dehydrated by means of a Whatman 1PS filter paper and then, concentrated in vacuo to thereby obtain 135 mg of compound 105B as a light yellow oily substance (yield: 100%).

EXAMPLE 6

Synthesis of 2-{N-[4-(2-thienylcarbonylamino) butyl]}aminomethyl-2,3-dihydrobenzo[b]furan (compound 106B)

Step A Synthesis of 2-{N-(tert-butoxycarbonyl)-N-[4-(2-thienylcarbonylamino)butyl]}aminomethyl-2,3-dihydrobenzo[b]furan (compound 106A)

160 mg (0.50 mmol) of compound 001H, which had been prepared in Step H of Reference Example 1, was dissolved in 1.6 ml of methylene chloride, followed by cooling to 0° C. To the resultant solution were added 0.14 ml (1.0 mmol) of triethylamine and 0.06 ml (0.6 mmol) of 2-thenoyl chloride (manufactured and sold by Tokyo Kasei Kogyo Co., Ltd., Japan). The resultant mixture was stirred at 0° C. for 3 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 106A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (200:1), to thereby obtain 213 mg of compound 106A as a light yellow oily substance (yield: 99%).

Step B Synthesis of 2-{N-[4-(2-thienylcarbonylamino) butyl]}aminomethyl-2,3-dihydrobenzo[b]furan (compound 106B)

200 mg (0.46 mmol) of compound 106A, which had been prepared in Step A, was cooled to 0° C. To the cooled compound was added 2.0 ml of trifluoroacetic acid and then, the resultant mixture was stirred at 0° C. for 5 hours to effect a reaction. The resultant reaction mixture was concentrated in vacuo to thereby obtain a residue, which was then dissolved in 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 106B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (25:1), to thereby obtain 133 mg of compound 106B as a light yellow oily substance (yield: 88%).

EXAMPLE 7

Synthesis of 2-{N-[4-(3-thienylcarbonylamino) butyl]}aminomethyl-2,3-dihydrobenzo[b]furan (compound 107B)

Step A Synthesis of 2-{N-(tert-butoxycarbonyl)-N-[4-(3-thienylcarbonylamino)butyl]}aminomethyl-2,3-dihydrobenzo[b]furan (compound 107A)

64 mg (0.50 mmol) of 3-thiophenecarboxylic acid was dissolved in 5.0 ml of methylene chloride, followed by cooling to −25° C. To the resultant solution were added 0.08 ml (0.6 mmol) of triethylamine and 0.08 ml (0.6 mmol) of isobutylchloroformate. The resultant mixture was stirred at −25° C. for 10 minutes to effect a reaction. To the resultant reaction mixture was added a solution of 192 mg (0.60 mmol) of compound 001H, which had been prepared in Step H of Reference Example 1, dissolved in 2.0 ml of methylene chloride. The resultant mixture was stirred at first at −25° C. for 10 minutes and then at room temperature for 4 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 107A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with chloroform, to thereby obtain 75 mg of compound 107A as a light yellow oily substance (yield: 35%).

Step B Synthesis of 2-{N-[4-(3-thienylcarbonylamino) butyl]}aminomethyl-2,3-dihydrobenzo[b]furan (compound 107B)

74 mg (0.17 mmol) of compound 107A, which had been prepared in Step A, was cooled to 0° C. To the cooled compound was added 0.13 ml of trifluoroacetic acid and then, the resultant mixture was stirred at 0° C. for 3.5 hours to effect a reaction. The resultant reaction mixture was concentrated in vacuo to thereby obtain a residue, which was then dissolved in 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 107B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (30:1), to thereby obtain 36 mg of compound 107B as a light yellow oily substance (yield: 64%).

EXAMPLE 8

Synthesis of 2-{N-[4-(2-furylcarbonylamino)butyl]} aminomethyl-2,3-dihydrobenzo[b]furan (compound 108B)

Step A Synthesis of 2-{N-(tert-butoxycarbonyl)-N-[4-(2-furylcarbonylamino)butyl]}aminomethyl- 2,3-dihydrobenzo[b]furan (compound 108A)

160 mg (0.50 mmol) of compound 001H, which had been prepared in Step H of Reference Example 1, was dissolved in 1.6 ml of methylene chloride, followed by cooling to 0° C. To the resultant solution were added 0.14 ml (1.0 mmol) of triethylamine and 0.06 ml (0.6 mmol) of 2-furoyl chloride (manufactured and sold by Tokyo Kasei Kogyo Co., Ltd., Japan). The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 108A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (200:1), to thereby obtain 204 mg of compound 108A as a light yellow oily substance (yield: 99%).

Step B Synthesis of 2-{N-[4-(2-furylcarbonylamino) butyl]}aminomethyl-2,3-dihydrobenzo[b]furan (compound 108B)

198 mg (0.48 mmol) of compound 108A, which had been prepared in Step A, was cooled to 0° C. To the cooled compound was added 2.0 ml of trifluoroacetic acid and then, the resultant mixture was stirred at 0° C. for 3 hours to effect a reaction. The resultant reaction mixture was concentrated in vacuo to thereby obtain a residue, which was then dissolved in 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 108B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (30:1), to thereby obtain 117 mg of compound 108B as a light yellow solid substance (yield: 78%).

EXAMPLE 9

Synthesis of 2-{N-[4-(3-furylcarbonylamino)butyl]}aminomethyl-2,3-dihydrobenzo[b]furan (compound 109B)

Step A Synthesis of 2-{N-(tert-butoxycarbonyl)-N-[4-(3-furylcarbonylamino)butyl]}aminomethyl-2,3-dihydrobenzo[b]furan (compound 109A)

112 mg (1.00 mmol) of 3-furancarboxylic acid was dissolved in 10 ml of methylene chloride, followed by cooling to −25° C. To the resultant solution were added 0.17 ml (1.2 mmol) of triethylamine and 0.16 ml (1.2 mmol) of isobutylchloroformate. The resultant mixture was stirred at −25° C. for 10 minutes to effect a reaction. To the resultant reaction mixture was added a solution of 192 mg (0.60 mmol) of compound 001H, which had been prepared in Step H of Reference Example 1, dissolved in 2.0 ml of methylene chloride. The resultant mixture was stirred at first at −25° C. for 10 minutes and then at room temperature for 3 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 109A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with chloroform, to thereby obtain 250 mg of compound 109A as a light yellow oily substance (yield: 61%).

Step B Synthesis of 2-{N-[4-(3-furylcarbonylamino)butyl]}aminomethyl-2,3-dihydrobenzo[b]furan (compound 109B)

242 mg (0.59 mmol) of compound 109A, which had been prepared in Step A, was cooled to 0° C. To the cooled compound was added 0.45 ml of trifluoroacetic acid and then, the resultant mixture was stirred at 0° C. for 3 hours to effect a reaction. The resultant reaction mixture was concentrated in vacuo to thereby obtain a residue, which was then dissolved in 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 109B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (25:1), to thereby obtain 135 mg of compound 109B as a light yellow oily substance (yield: 73%).

EXAMPLE 10

Synthesis of the hydrochloride of (+)-2-{N-[4-(2-thienylcarbonylamino)butyl]}aminomethyl-2,3-dihydrobenzo[b]furan (compound 110A)

803 mg (2.43 mmol) of compound 106B, which had been prepared in Example 6, was dissolved in 10 ml of methanol. To the resultant solution was added 839 mg (2.43 mmol) of (R)-(−)-N-(3,5-dinitrobenzoyl)-α-phenylglycine (manufactured and sold by Tokyo Kasei Kogyo Co., Ltd., Japan). The resultant mixture was allowed to stand still at room temperature for 24 hours to thereby deposit crystals. The crystals were collected by filtration, followed by drying in vacuo. The crystals were recrystallized twice from methanol to thereby obtain 208 mg of crystals. The obtained crystals were dissolved in 2 ml of a 0.5N aqueous sodium hydroxide solution, followed by extraction twice with 10 ml of chloroform, to thereby form a chloroform layer containing (+)-2-{N-[4-(2-thienylcarbonylamino)butyl]}aminomethyl-2,3-dihydrobenzo[b]furan, followed by separation of the chloroform layer. The chloroform layer thus separated was successively washed with 10 ml of water and 10 ml of saturated saline and then, dehydrated by means of a Whatman 1PS filter paper and then, concentrated in vacuo to thereby obtain a residue. The obtained residue was dissolved in a 2.7N solution of hydrochloric acid in methanol and then, concentrated in vacuo to thereby deposit crystals. The crystals were collected by filtration and dried in vacuo to obtain 105 mg of compound 110A as white crystals.

Optical purity: 97.7% e.e. as measured using Chiral cell OD (column size: 0.46×25 cm) manufactured by Osaka Soda Co., Ltd., Japan, elution solvent: hexane-ethanol=90:10 (including 0.1% triethylamine), elution speed: 0.6 ml/min, and detection wavelength: 270 nm $[\alpha]_D$ 62.0 (c=0.26, methanol)

EXAMPLE 11

Synthesis of the hydrochloride of (−)-2-{N-[4-(2-thienylcarbonylamino)butyl]}aminomethyl-2,3-dihydrobenzo-[b]furan (compound 111A)

All mother liquors, which had been used for crystallization and recrystallization in Example 10, were collected and then, concentrated in vacuo. The resultant mixture was dissolved in 10 ml of a 1N aqueous sodium hydroxide solution, followed by extraction twice with 10 ml of chloroform, to thereby form a chloroform layer containing (−)-2-{N-[4-(2-thienylcarbonylamino)butyl]aminomethyl-2,3-dihydrobenzo[b]furan, followed by separation of the chloroform layer. The chloroform layer thus separated was successively washed with 10 ml of water and 10 ml of saturated saline and then, dehydrated by means of a Whatman 1PS filter paper and then, concentrated in vacuo to thereby obtain a light yellow oily substance. The obtained substance was dissolved in 25 ml of methanol. To the resultant solution was added 733 mg (2.12 mmol) of (S)-(+)-N-(3,5-dinitrobenzoyl)-α-phenylglycine (manufactured and sold by Aldrich Chemical Co., Inc., U.S.A.). The resultant reaction mixture was allowed to stand still at room temperature for 24 hours to thereby deposit crystals. The crystals were collected by filtration, and dried in vacuo. The crystals were recrystallized twice from methanol to obtain 205 mg of crystals. The obtained crystals were dissolved in 2 ml of a 0.5N aqueous sodium hydroxide solution, followed by extraction twice with 10 ml of chloroform, to thereby form a chloroform layer, followed by separation of the chloroform layer. The chloroform layer thus separated was successively washed with 10 ml of water and 10 ml of saturated saline and then, dehydrated by means of a Whatman 1PS filter paper and then, concentrated in vacuo to thereby obtain a residue. The obtained residue was dissolved in a 2.0N solution of hydrochloric acid in methanol and then, concentrated in vacuo to thereby deposit crystals. The crystals were collected by filtration, and dried in vacuo to obtain 100 mg of compound 111A as white crystals.

Optical purity: 97.7% e.e. as measured using Chiral cell OD (column size: 0.46×25 cm) manufactured by Osaka Soda Co., Ltd., Japan, elution solvent: hexane-ethanol=90:10 (including 0.1% triethylamine), elution speed: 0.6 ml/min, and detection wavelength: 270 nm $[\alpha]_D$ −62.9 (c=0.25, methanol)

EXAMPLE 12

Synthesis of 2-{N-[2-(1-naphthoylamino)ethyl]}aminomethyl-2,3-dihydrobenzo[b]furan (compound 112B)

Step A Synthesis of 2-{N-benzyl-N-[2-(1-naphthoylamino)ethyl]}aminomethyl-2,3-dihydrobenzo[b]furan (compound 112A)

141 mg (0.50 mmol) of compound 002C, which had been prepared in in Reference Example 2, was dissolved in 2.0 ml of methylene chloride, followed by cooling to 0° C. To the resultant solution were added 0.14 ml (1.00 mmol) of triethylamine and 0.09 ml (0.6 mmol) of 1-naphthoyl chloride. The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 112A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (3:1), to thereby obtain 179 mg of compound 112A as a light yellow oily substance (yield: 82%).

Step B Synthesis of 2-{N-[2-(1-naphthoylamino)ethyl]}aminomethyl-2,3-dihydrobenzo[b]furan (compound 112B)

175 mg (0.40 mmol) of compound 112A, which had been prepared in Step A, was dissolved in 2.0 ml of methylene chloride, followed by cooling to 0° C. To the resultant solution was added 0.71 ml (1.20 mmol) of a solution of benzyloxycarbonyl chloride in toluene (which solution was manufactured and sold by Tokyo Kasei Kogyo Co., Ltd., Japan) and then, the resultant mixture was stirred at 40° C. for 6 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (1:1), to thereby obtain 168 mg of 2-{N-carbobenzoxy-N-[2-(1-naphthoylamino)ethyl]}aminomethyl-2,3-dihydrobenzo[b]furan as a white bubbly substance.

The obtained compound was dissolved in 0.5 ml of acetic acid. To the resultant solution was added 0.05 ml of anisole, followed by cooling to 0° C. and then 0.84 ml of a solution of 30% hydrobromic acid in acetic acid was added thereto. The resultant mixture was stirred at room temperature for 1 hour to effect a reaction. The resultant reaction mixture was added 20 ml of diethyl ether to deposit a precipitate. The precipitate was collected by filtration. The collected precipitate was dissolved in 20 ml of chloroform and then, the resultant solution was successively washed with 20 ml of a saturated aqueous sodium hydrogencarbonate solution, 20 ml of water and 20 ml of saturated saline, to thereby form a chloroform layer containing the desired compound 112B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (20:1), to thereby obtain 112 mg of compound 112B as a transparent oily substance (yield: 81%).

EXAMPLE 13

Synthesis of 2-{N-[3-(1-naphthoylamino)propyl]}aminomethyl-2,3-dihydrobenzo[b]furan (compound 113B)

Step A Synthesis of 2-{N-benzyl-N-[3-(1-naphthoylamino)propyl]}aminomethyl-2,3-dihydrobenzo[b]furan (compound 113A)

148 mg (0.50 mmol) of compound 003B, which had been prepared in Reference Example 3, was dissolved in 2.0 ml of methylene chloride, followed by cooling to 0° C. To the resultant solution were added 0.14 ml (1.0 mmol) of triethylamine and 0.09 ml (0.6 mmol) of 1-naphthoyl chloride. The resultant mixture was stirred at 0° C. for 2 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 113A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (3:1), to thereby obtain 219 mg of compound 113A as a transparent oily substance (yield: 97%).

Step B Synthesis of 2-{N-[3-(1-naphthoylamino)propyl]}aminomethyl-2,3-dihydrobenzo[b]furan (compound 113B)

255 mg (0.57 mmol) of compound 113A, which had been prepared in Step A, was dissolved in 3.0 ml of methylene chloride, followed by cooling to 0° C. To the resultant solution was added 1.0 ml (1.7 mmol) of a solution of benzyloxycarbonyl chloride in toluene (which solution was manufactured and sold by Tokyo Kasei Kogyo Co., Ltd., Japan) and then, the resultant mixture was stirred at 40° C. for 6 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer, followed by separation of the chloroform layer. The chloroform layer thus separated was dehydrated by means of a Whatman 1PS filter paper and then, concentrated in vacuo to thereby obtain a residue. The obtained residue was purified-by silica gel column chromatography. That is, the residue was applied to a column of 10 g of silica gel (Art. 9385, manufactured and sold by E. Merck, Darmstadt, Germany) and eluted with a mixed solvent of hexane-ethyl acetate (2:1), to thereby obtain 2-{N-carbobenzoxy-N-[3-(1-naphthoylamino)propyl]}aminomethyl-2,3-dihydrobenzo[b]furan as a white bubbly substance.

The obtained compound was dissolved in 0.7 ml of acetic acid. To the resultant solution was added 0.07 ml of anisole, followed by cooling to 0° C. and then 1.2 ml of a solution of 30 % hydrobromic acid in acetic acid was added thereto. The resultant mixture was stirred at room temperature for 1 hour to effect a reaction. The resultant reaction mixture was added 20 ml of diethyl ether to deposit precipitate. The precipitate was collected by filtration. The collected precipitate was dissolved in 20 ml of chloroform and then, the resultant solution was successively washed with 20 ml of a saturated aqueous sodium hydrogencarbonate solution, 20 ml of water and 20 ml of saturated saline, to thereby form a chloroform layer containing the desired compound 113B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (10:1), to thereby obtain 171 mg of compound 113B as a transparent oily substance (yield: 83%).

EXAMPLE 14

Synthesis of 2-{N-[4-(1-naphthylsulfonylamino)butyl]}aminomethyl-2,3-dihydrobenzo[b]furan (compound 114B)

Step A Synthesis of 2-{N-(tert-butoxycarbonyl)-N-[4-(1-naphthylsulfonylamino)butyl]}aminomethyl-2,3-dihydrobenzo[b]furan (compound 114A)

160 mg (0.50 mmol) of compound 001H, which had been prepared in Step H of Reference Example 1, was dissolved in 2.0 ml of methylene chloride, followed by cooling to 0° C. To the resultant solution were added 0.14 ml (1.0 mmol) of triethylamine and 136 mg (0.60 mmol) of 1-naphthalenesulfonyl chloride (manufactured and sold by Tokyo Kasei Kogyo Co., Ltd., Japan). The resultant mixture was stirred at 0° C. for 6 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 114A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with chloroform, to thereby obtain 269 mg of compound 114A as a light yellow oily substance (yield: 100 0%).

Step B Synthesis of 2-{N-[4-(1-naphthylsulfonylamino)butyl]}aminomethyl-2,3-dihydrobenzo[b]furan (compound 114B)

246 mg (0.48 mmol) of compound 114A, which had been prepared in Step A, was dissolved in 5.0 ml of methylene chloride, followed by cooling to 0° C. To the resultant solution was added 0.37 ml of trifluoroacetic acid and then, the resultant mixture was stirred at 0° C. for 3 hours to effect a reaction. The resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 114B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (50:1), to thereby obtain 163 mg of compound 114B as a light yellow oily substance (yield: 83%).

EXAMPLE 15

Synthesis of 2-{N-[4-(2-naphthylsulfonylamino)butyl]}aminomethyl-2,3-dihydrobenzo[b]furan (compound 115B)

Step A Synthesis of 2-{N-(tert-butoxycarbonyl)-N-[4-(2-naphthylsulfonylamino)butyl]}aminomethyl-2,3-dihydrobenzo[b]furan (compound 115A)

160 mg (0.50 mmol) of compound 001H, which had been prepared in Step H of Reference Example 1, was dissolved in 2.0 ml of methylene chloride, followed by cooling to 0° C. To the resultant solution were added 0.14 ml (1.0 mmol) of triethylamine and 136 mg (0.60 mmol) of 2-naphthalenesulfonyl chloride (manufactured and sold by Tokyo Kasei Kogyo Co., Ltd., Japan). The resultant mixture was stirred at 0° C. for 3 hours to effect a reaction. To the resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 115A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with chloroform, to thereby obtain 252 mg of compound 115A as a light yellow oily substance (yield: 99%).

Step B Synthesis of 2-{N-[4-(2-naphthylsulfonylamino) butyl]}aminomethyl-2,3-dihydrobenzo[b]furan (compound 115B)

242 mg (0.48 mmol) of compound 115A, which had been prepared in Step A, was dissolved in 5.0 ml of methylene chloride, followed by cooling to 0° C. To the resultant solution was added 0.37 ml of trifluoroacetic acid and then, the resultant mixture was stirred at 0° C. for 4 hours to effect a reaction. The resultant reaction mixture was added 20 ml of chloroform to obtain a mixture. The obtained mixture was successively washed with 20 ml of a saturated aqueous sodium hydrogencarbonate solution, 20 ml of water and 20 ml of saturated saline, to thereby form a chloroform layer containing the desired compound 115B, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (50:1), to thereby obtain 170 mg of compound 115B as a light yellow oily substance (yield: 87%).

EXAMPLE 16

Synthesis of the hydrochloride of (−)-2-{N-methyl-N-[4-(2-thienylcarbonylamino)butyl]}aminomethyl-2,3-dihydrobenzo[b]furan (compound 116A)

73 mg (0.22 mmol) of (−)-2-{N-[4-(2-thienylcarbonylamino)butyl]}aminomethyl-2,3-dihydrobenzo[b]furan, which had been prepared in substantially the same manner as in Example 11 except that the obtained residue was not dissolved in a solution of hydrochloric acid in methanol, was dissolved in 1.5 ml of methanol. To the resultant solution were added 0.20 ml (2.5 mmol) of a solution of 37% formaldehyde and 16 mg (0.25 mmol) of sodium borohydride. The resultant mixture was stirred at 0° C. for 2 hours to effect a reaction. To the resultant reaction mixture was added 20 ml of chloroform to obtain a mixture. The obtained mixture was successively washed with 20 ml of water and 20 ml of saturated saline, to thereby form a chloroform layer containing the desired compound 116A, followed by separation of the chloroform layer. The chloroform layer thus separated was dehydrated by means of a Whatman 1PS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (30:1), to thereby obtain 63 mg of a light yellow oily substance. The obtained substance was dissolved in a 2.7N solution of hydrochloric acid in methanol and then, concentrated in vacuo to thereby deposit crystals. The crystals were collected by filtration and dried in vacuo to obtain 60 mg of compound 116A as white crystals.

$[\alpha]_D$ −57.3 (c=0.26, methanol)

EXAMPLE 17

Synthesis of the hydrochloride of (−)-2-{N-ethyl-N-[4-(2-thienylcarbonylamino)butyl]}aminomethyl-2,3-dihydrobenzo[b]furan (compound 117A)

83 mg (0.25 mmol) of (−)-2-{N-[4-(2-thienylcarbonylamino)butyl]}aminomethyl-2,3-dihydrobenzo[b]furan, which had been prepared in substantially the same manner as in Example 11 except that the obtained residue was not dissolved in a solution of hydrochloric acid in methanol, was dissolved in 0.8 ml of acetonitrile. To the resultant solution were added 0.024 ml (0.30 mmol) of ethyl iodide and 70 mg (0.50 mmol) of potassium carbonate. The resultant mixture was stirred at 80° C. for 2 hours to effect a reaction. To the resultant reaction mixture was added 20 ml of chloroform to obtain a mixture. The obtained mixture was successively washed with 20 ml of water and 20 ml of saturated saline, to thereby form a chloroform layer, followed by separation of the chloroform layer. The chloroform layer thus separated was dehydrated by means of a Whatman UPS filter paper and then, concentrated in vacuo to thereby obtain a residue. The obtained residue was purified by silica gel column chromatography. That is, the residue was applied to a column of 10 g of silica gel (Art. 9385, manufactured and sold by E. Merck, Darmstadt, Germany) and eluted with a mixed solvent of chloroform-methanol (30:1), to thereby obtain 66 mg of a light yellow oily substance. The obtained substance was dissolved in a 2.7N solution of hydrochloric acid in methanol and then, concentrated in vacuo to deposit crystals. The crystals were collected by filtration and dried in vacuo to obtain 62 mg of compound 117A as a light yellow bubbly substance.

$[\alpha]_D$ −54.5 (c=0.22, methanol)

TABLE 4

| Compound No. | $^1$H-NMR ($CDCL_3$) δ (ppm) | MASS (FAB) |
|---|---|---|
| 001 A | 2.29 (3H, s), 3.30 (2H, d, J = 6.6Hz), 5.00~5.10 (2H, m), 5.80~6.00 (1H, m) 7.15~7.30 (4H, m) | 176 (MH$^+$) |
| 001 B | 2.36 (3H, s), 2.86 (1H, dd, J = 14.5Hz, 9.2Hz), 3.63 (1H, dd, J = 14.5Hz, 4.3Hz), 3.67 (1H, t, J = 10.0Hz), 3.89 (1H, dd, J = 10.2Hz, 3.9Hz), 4.25~4.35 (1H, m) | 337 (MH$^+$) |
| 001 C | 3.12 (1H, dd, J = 15.8Hz, 6.5Hz), 3.35~3.65 (3H, m), 4.95~5.05 (1H, m), 6.79 (1H, d, J = 7.9Hz), 6.87 (1H, t, J = 7.5Hz), 7.10~7.20 (2H, m) | 212 (M$^+$) |
| 001 D | 1.60~1.75 (5H, m), 2.65~3.00 (1H, dd, J = 15.5Hz, 9.2Hz), 3.60 (2H, t, J = 5.0Hz), 4.85~5.00 (1H, m), 6.76 (1H, d, J = 7.9Hz), 6.84 (1H, t, J = 7.2Hz), 7.05~7.20 (2H, m) | 222 (MH$^+$) |
| 001 E | 1.40~1.60 (4H, m), 1.46 (9H, s), 2.89 (1H, dd, J = 15.8 Hz, 7.3Hz), 3.20~3.65 (7H, m), 5.00 (1H, brs), 6.76 (1H, d, J = 7.9Hz), 6.84 (1H, t, J = 7.5Hz), 7.00~7.20 (2H, m) | 322 (MH$^+$) 222 |

TABLE 4-continued

| Compound No. | $^{1}$H-NMR (CDCL$_3$) δ (ppm) | MASS (FAB) |
|---|---|---|
| 001 F | 1.40~1.75 (4H, m), 1.44 (9H, s), 2.44 (3H, s), 2.86 (1H, H, dd, J = 15.8Hz, 7.2Hz), 3.20~3.70 (5H, m), 4.05 (2H, t, J = 5.9Hz), 4.95 (1H, brs), 6.73 (1H, d, J = 7.6Hz), 6.84 (1H, t, J = 7.5Hz), 7.05~7.20 (2H, m), 7.33 (2H, d, J = 8.3Hz), 7.78 (2H, d, J = 8.3Hz) | 476 (MH$^{+}$) 376 |
| 001 G | 1.40~1.70 (4H, m), 1.47 (9H, s), 2.89 (1H, dd, J = 15.8 Hz, 7.3Hz), 3.20~3.75 (7H, m), 5.00 (1H, brs), 6.76 (1H, d, J = 7.9Hz), 6.84 (1H, t, J = 7.4Hz), 7.00~7.20 (2H, H, m) | 347 (MH$^{+}$) 247 |
| 001 H | not measured | 321 (MH$^{+}$) 221 |
| 002 A | 1.70 (1H, s), 2.85~3.05 (3H, m), 3.25 (1H, dd, J = 15.5Hz, 9.2 Hz), 3.86 (2H, s), 4.90~5.00 (1H, m), 6.75~6.90 (2H, m), 7.05~7.20 (2H, m), 7.20~7.40 (5H, m) | 240 (MH$^{+}$) |
| 002 B | 2.70~3.00 (5H, m), 3.10 (1H, dd, J = 15.5Hz, 9.2Hz), 3.65~3.90 (4H, m), 4.80~4.95 (1H, m), 6.66 (1H, d, J = 7.9Hz), 6.70~6.80 (1H, m), 7.00~7.30 (7H, m), 7.65~7.75 (2H, m), 7.75~7.85 (2H, m) | 413 (MH$^{+}$) |
| 002 C | 1.63 (2H, s), 2.60~2.95 (7H, m), 3.22 (1H, dd, J = 15.7Hz, 9.1Hz), 3.72 (1H, d, J = 13.7Hz), 3.75 (1H, d, J = 13.7Hz), 4.85~5.00 (1H, m) 6.76 (1H, d, J = 7.9Hz), 6.75~6.85 (1H, m), 7.05~7.20 (2H, m), 7.20~7.35 (5H, m) | 283 (MH$^{+}$) |
| 003 A | 1.80~1.95 (2H, m), 2.55~2.90 (4H, m), 2.95 (1H, dd, J = 15.7Hz, 7.4Hz), 3.21 (1H, dd, J = 15.7Hz, 9.1Hz), 3.60~3.80 (4H, m), 4.80~4.95 (1H, m), 6.69 (1H, d, J = 7.9Hz), 6.79 (1H, dd, J = 7.6Hz, 7.3Hz), 7.00~7.40 (7H, m), 7.65~7.75 (2H, m), 7.80~7.90 (2H, m) | 427 (MH$^{+}$) |
| 003 B | 1.53 (2H, s), 1.55~1.70 (2H, m), 2.50~2.75 (5H, m), 2.82 (1H, dd, J = 13.5 Hz, 6.3Hz), 2.92 (1H, dd, J = 15.5Hz, 7.6Hz), 3.20 (1H, dd, J = 15.5Hz, 9.1Hz), 3.64 (1H, d, J = 13.7Hz), 3.73 (1H, d, J = 13.7Hz), 4.80~4.95 (1H, m), 6.75 (1H, dd, J = 7.9Hz), 6.81 (1H, dd, J = 7.6Hz, 7.3Hz), 7.00~7.15 (2H, m), 7.20~7.35 (5H, m) | 297 (MH$^{+}$) |
| 101 A | 1.45 (9H, s), 1.55~1.80 (4H, m), 2.88 ( 1H, dd, J = 15.8Hz, 7.3Hz), 3.20~3.80 (7H, m), 4.96 (1H, brs), 6.70~6.90 (2H, m), 7.05~7.20 (3H, m), 7.40~7.65 (4H, m), 7.80~7.95 (2H, m), 8.25~8.35 (1H, m) | 475 (MH$^{+}$) 375 |
| 101 B | 1.60~1.80 (5H, m), 2.55~2.65 (1H, m), 2.70~2.80 (4H, m), 3.00~3.10 (1H, m), 3.45~3.65 (2H, m) 4.50~4.65 (1H, m), 6.71 (1H, d, J = 7.9Hz), 6.81 (1H, t, J = 7.6Hz), 7.05 (1H, brs), 7.08 (2H, t, J = 7.6Hz), 7.40~7.60 (4H, m), 7.80~7.90 (2H, m), 8.25~8.30 (1H, m) | 375 (M$^{+}$) |
| 102 A | 1.47 (9H, s), 1.60~1.80 (4H, m), 2.88 (1H, dd, J = 15.7Hz, 7.1Hz), 3.20~3.70 (7H, m), 4.98 (1H, brs), 6.74 (1H, d, J = 8.3Hz), 6.83 (1H, t, J = 7.3Hz), 7.00~7.20 (3H, m), 7.50~7.65 (2H, m), 7.80~7.95 (4H, m), 8.20~8.40 (1H, m) | 475 (MH$^{+}$) 375 |
| 102 B | 1.65~1.80 (5H, m), 2.76 (2H, t, J = 6.6Hz), 2.80~2.95 (3H, m), 3.15~3.25 (1H, m), 3.50~3.60 (2H, m), 4.85~4.95 (1H, m), 6.76 (1H, d, J = 7.9Hz), 6.82 (1H, t, J = 7.6Hz), 7.05~7.15 (3H, m), 7.45~7.60, (2H, m), 7.80~7.95 (4H, m), 8.28 (1H, s) | 375 (MH$^{+}$) |
| 103 A | 1.47 (9H, s), 1.55~1.80 (4H, m), 2.88 (1H, dd, J = 15.8Hz, 6.9Hz), 3.20~3.65 (7H, m), 4.97 (1H, brs), 6.75 (1H, d, J = 7.3Hz), 6.85 (1H, t, J = 7.3Hz), 7.05~7.20 (3H, m), 7.57 (1H, brs), 7.75 (1H, brs), 8.71 (2H, d, J = 5.6Hz) | 426 (MH$^{+}$) 326 |
| 103 B | 1.60~18.0 (5H, m), 2.76 (2H, t, J = 6.3Hz), 2.80~2.95 (3H, m), 3.20~3.30 (1H, m), 3.45~3.55 (2H, m), 4.80~4.95 (1H, m), 6.76 (1H, d, J = 7.9Hz), 6.84 (1H, t, J = 7.6Hz), 7.10 (1H, d, J = 7.6Hz), 7.15 (1H, d, J = 6.9Hz), 7.47 (1H, brs), 7.61 (2H, dd, J = 4.6Hz, 3.0Hz), 8.69 (2H, dd, J = 4.6Hz, 3.0Hz) | 326 (MH$^{+}$) |
| 104 A | 1.46 (9H, s), 1.55~1.75 (4H, m), 2.80~2.95 (1H, m), 3.20~3.60 (7H, m), 4.96, (1H, brs), 6.74 (1H, d, J = 7.6Hz), 6.84 (1H, t, J = 7.3Hz), 7.00~7.20 (2H, m), 7.30~7.50 (2H, m), 8.10~8.25 (1H, m), 8.65~8.75 (1H, m), 8.95~9.15 (1H, m) | 426 (MH$^{+}$) 326 |
| 104 B | 1.55~1.80 (5H, m), 2.70~3.00 (5H, m), 3.25 (1H, dd, J = 15.5Hz, 9.2Hz), 3.40~3.60 (2H, m), 4.80~4.95 (1H, m), 6.74 (1H, d, J = 7.9Hz), 6.80~6.90 (1H, m), 7.05~7.20 (1H, m), 7.34 (1H, dd, J = 7.8Hz, 5.0Hz), 7.44 (1H, brs), 8.10~8.15 (1H, m), 8.68 (1H, dd, J = 5.0Hz, 1.7Hz), 8.95~9.05 (1H, m) | 326 (MH$^{+}$) |
| 105 A | 1.45 (9H, s), 1.55~1.70 (4H, m), 2.88 (1H, dd, J = 15.8Hz, 6.9Hz), 3.20~3.60, (7H, m) m), 4.99 (1H, brs), 6.75 (1H, d), J = 7.9Hz), 6.83 (1H, t, J = 7.4Hz), 7.05~7.20 (2H, m), 7.35~7.45 (1H, m), 7.84 (1H, dt, J = 7.6Hz, 1.7Hz, 8.09 (1H, brs), 8.19 (1H), d, J = 7.9Hz), 8.50~8.55 (1H, m) | 426 (MH$^{+}$) 326 |

TABLE 4-continued

| Compound No. | $^1$H-NMR (CDCL$_3$) δ (ppm) | MASS (FAB) |
|---|---|---|
| 105 B | 1.55~1.70 (5H, m), 2.60~2.70 (2H, m), 2.75~2.95, (3H, m), 3.20 (1H, dd, J = 15.5Hz, 9.2Hz), 3.40~3.50 (2H, m), 4.80~4.95 (1H, m), 6.69 (1H, d, J = 7.9Hz), 6.70~6.80 (1H, m), 7.00~7.10 (2H, m), 7.34 (1H, ddd, J = 7.6Hz, 4.6Hz, 1.3Hz), 7.70~7.80 (1H, m), 8.10~8.20 (1H, m) | 326 (MH$^+$) |
| 106 A | 1.46 (9H, s), 1.55~1.75 (4H, m), 2.88 (1H, dd, J = 15.8Hz, 6.9Hz), 3.20~3.55 (7H, m), 4.97 (1H, brs), 6.75 (1H, d, J = 7.9Hz), 6.80~6.90 (1H, m), 6.84 (1H, t, J = 7.3Hz), 7.00~7.20 (3H, m), 7.40~7.50 (2H, m) | 431 (MH$^+$) 331 |
| 106 B | 1.60~1.75 (5H, m), 2.75 (2H, t, J = 6.3Hz), 2.85~3.00 (3H, m), 3.28 (1H, dd, J = 15.5Hz, 9.2Hz), 3.45 (2H, dd, J = 12.2Hz, 6.3Hz), 4.85~5.00 (1H, m), 6.77 (1H, d, J = 7.9Hz), 6.83 (1H, t, J = 7.3Hz), 6.85 (1H, brs), 7.00~7.20 (3H, m), 7.43 (1H, dd, J = 5.0Hz, 0.7Hz), 7.49 (1H, dd, J = 3.5Hz, 0.7Hz) | 331 (MH$^+$) |
| 107 A | 1.46 (9H, s), 1.55~1.65 (4H, m), 2.88 (1H, dd, J = 15.8Hz, 6.9Hz), 3.15~3.55 (7H, m), 4.95 (1H, brs), 6.70~6.80 (1H, m), 6.80~6.90 (1H, m), 7.05~7.20 (3H, m), 7.30 (1H, brs), 7.50 (1H, brs), 7.95 (1H, brs) | 431 (MH$^+$) 331 |
| 107 B | 1.60~1.75 (5H, m), 2.70~2.80 (2H, m), 2.85~3.00 (3H, m), 3.20~3.35 (1H, m), 3.40~3.50 (2H, m), 4.85~5.00 (1H, m), 6.66 (1H, brs), 6.77 (1H, d, J = 7.9Hz), 6.80~6.90 (1H, m), 7.05~7.20 (1H, m), 7.30 (1H, dd, J = 5.0Hz, 3.0Hz), 7.37 (1H, dd, J = 5.0Hz, 1.3Hz), 7.80~7.85 (1H, m) | 331 (MH$^+$) |
| 108 A | 1.46 (9H, s), 1.50~1.75 (4H, m), 2.88 (1H, dd, J = 15.8 Hz, 6.9Hz), 3.20~3.50 (7H, m), 4.98 (1H, brs), 6.45~6.50 (1H, m), 6.75 (1H, d, J = 7.9Hz), 6.84 (1H, t, J = 7.3Hz), 7.05~7.20 (3H, m), 7.40~7.45 (1H, m) | 415 (MH$^+$) 315 |
| 108 B | 1.60~1.75 (5H, m), 2.73 (1 H, t, J = 6.6Hz), 2.85~3.00 (3H, m), 3.28 (1H, dd, J = 15.5Hz, 9.2Hz), 3.45 (2H, dd, J = 12.5Hz, 6.3Hz), 4.90~5.00 (1H, m), 6.45~6.50 (1H, m), 6.77 (1H, d, J = 7.9Hz), 6.83 (1H, t, J = 7.3Hz), 6.85 (1H, brs), 7.10~7.25 (3H, m), 7.35~7.40 (1H, m) | 315 (MH$^+$) |
| 109 A | 1.47 (9H, s), 1.55~1.70 (4H, m), 2.88 (1H, dd, J = 15.8Hz, 6.9Hz), 3.20~3.55 (7H, m), 4.96 (1H, brs), 6.70~6.90 (3H, m), 7.05~7.20 (2H, m), 7.41 (1H, s), 7.90~8.05 (2H, m) | 415 (MH$^+$) 315 |
| 109 B | 1.55~1.75 (5H, m), 2.70~2.75 (2H, m), 2.80~3.00 (2H, m), 3.20~3.35 (1H, m), 3.40~3.50 (2H, m), 4.85~5.00 (1H, m), 6.47 (1H, brs), 6.59 (1H, s), 6.76 (1H, d, J = 7.9Hz), 6.80~6.90 (1H, m), 7.05~7.20 (2H, m), 7.39 (1H, s), 7.90 (1H, s) | 343 (MH$^+$) |
| 110 | NMR spectra for this compound (in the form of tree base) are the same of those of compound 106B | 331 (MH$^+$) |
| 111 | NMR spectra for this compound (in the form of tree base) are the same of those of compound 106B | 331 (MH$^+$) |
| 112 A | 2.70~2.95 (5H, m), 3.14 (1H, dd, J = 15.5Hz, 9.2Hz), 3.40~3.55 (1H, m), 3.60~3.80 (1H, m), 3.72 (1H, d, J = 13.7Hz), 3.80 (1H, d, J = 13.7Hz), 4.80~4.95 (1H, m), 6.38 (1H, d, J = 7.9Hz), 6.70~6.80 (2H, m), 6.90~7.05 (2H, m), 7.15~7.30 (5H, m), 7.40~7.55 (4H, m), 7.85~7.95 (2H, m), 8.30~8.40 (1H, m) | 437 (MH$^+$) |
| 112 B | 1.60 (1H, s), 2.85~3.05 (5H, m), 3.23 (1H, dd, J = 15.5Hz, 9.2Hz), 3.60~3.70 (2H, m), 4.85~4.95(1H, m), 6.61 (1H, brs), 6.70 (1H, d, J = 7.9Hz), 6.75~6.85 (1H, m), 7.00~7.15 (2H, m), 7.40~7.65 (4H, m), 7.85~7.95 (2H, m), 8.30~8.40 (1H, m) | 347 (MH$^+$) |
| 113 A | 1.80~1.95 (2H, m), 2.60~2.90 (5H, m), 3.08 (1H, dd, J = 15.5Hz, 9.2Hz), 3.50~3.75 (4H, m), 4.75~4.90 (1H, m), 6.38 (1H, d, J = 7.6Hz), 6.57~7.20 (9H, m), 7.35~7.60 (4H, m), 7.85~7.95 (2H, m), 8.25~8.35 (1H, m) | 451 (MH$^+$) |
| 113 B | 1.57 (1H, s), 1.80~1.95 (2H, m), 2.70~2.95 (5H, m), 3.02 (1H, dd, J = 15.5Hz, 9.2Hz), 3.60~3.70 (2H, m), 4.65~4.80 (1H, m), 6.67 (1H, d, J = 7.9Hz), 6.78 (1H, t, J = 7.4Hz), 7.00~7.15 (2H, m), 7.40~7.65 (5H, m), 7.85~7.95 (2H, m), 8.30~8.40 (1H, m) | 361 (MH$^+$) |
| 114 A | 1.30~1.50 (13H, m), 2.75~3.60 (8H, m), 4.89 (1H, brs), 6.74 (1H, brs), 6.85 (1H, t, J = 7.3Hz), 7.09 (1H, d, J = 7.6Hz), 7.16 (1H, d, J = 7.3Hz), 7.52 (1H, t, J = 7.6Hz), 7.65~7.80 (2H, m), 7.92 (1H, d, J = 7.6Hz), 8.04 (1H, d, J = 8.3Hz), 8.25 (1H, dd, J = 7.3Hz, 1.0Hz), 8.63 (1H, brs) | 511 (MH$^+$) 411 |
| 114 B | 1.35~1.55 (5H, m), 2.50~2.70 (2H, m), 2.80~3.00 (5H, m), 3.33 (1H, dd, J = 15.8Hz, 9.2Hz), 4.95~5.10 (1H, m), 6.79 (1H, d, J = 7.9Hz), 6.85 (1H, t, J = 7.3Hz), 7.14 (1H, d, J = 7.9Hz), 7.17 (1H, t, J = 7.6Hz), 7.53 (1H, t, J = 7.6Hz), 7.55~7.70 (2H, | 411 (MH$^+$) |

TABLE 4-continued

| Compound No. | $^1$H-NMR (CDCL$_3$) δ (ppm) | MASS (FAB) |
|---|---|---|
| | m), 7.94 (1H, d, J = 7.6Hz), 8.04 (1H, d, J = 8.3Hz), 8.26 (1H, dd, J = 7.3Hz, 1.3Hz), 8.71 (1H, d, J = 8.6Hz) | |
| 115 A | 1.35~1.70 (13H, m), 2.80~2.90 (1H, m), 2.95~3.10 (2H, m), 3.15~3.50 (5H, m), 4.91 (1H, brs), 6.65~6.80 (1H, m), 6.83 (1H, t, J = 7.3Hz), 7.00~7.20 (3H, m), 7.55~7.70 (2H, m), 7.80~8.00 (4H, m), 8.42 (1H, s) | 511 (MH$^+$) 411 |
| 115 B | 1.35~1.70 (5H, m), 2.50~2.60 (1H, m), 2.65~2.75 (1H, m), 2.80~2.95 (4H, m), 3.00~3.10 (1H, m), 3.33 (1H, dd, J = 15.5Hz, 9.2Hz), 5.00~5.10 (1H, m), 6.78 (1H, d J = 7.9Hz), 6.85 (1H, t, J = 7.3Hz), 7.11 (1H, d, J = 7.6Hz, 7.17 (1H, t, J = 7.3Hz), 7.55~7.70 (2H, m), 7.80~8.00 (4H, m), 8.42 (1H, s) | 411 (MH$^+$) |
| 116 A | 1.50~1.75 (4H, m), 2.34 (3H, s), 2.45~2.60 (3H, m), 2.78 (1H, dd, J = 13.2Hz, 7.9Hz), 2.90 (1H, dd, J = 15.5Hz, 7.6Hz), 3.27 (1H, dd, J = 15.5Hz, 9.2Hz), 3.40~3.50 (2H, m), 4.85~5.00 (1H, m), 6.70~6.90 (3H, m), 7.00~7.20 (3H, m), 7.40~7.45 (1H, m), 7.50 (1H, d, J = 3.6Hz) | 345 (MH$^+$) |
| 117 A | 1.02 (3H, t, J = 7.1Hz), 1.45~1.70 (4H, m), 2.50~2.70 (5H, m), 2.81 (1H, dd, J = 13.7Hz, 7.4Hz), 2.93 (1H, dd J = 15.5Hz, 7.6Hz) 3.25 (1H, dd, J = 15.5Hz, 9.1Hz), 3.40~3.50 (2H, m), 4.85~5.00 (1H, m), 6.46 (1H, brs), 6.75 (1H, d, J = 7.9Hz), 6.75~6.90 (1H, m), 7.00~7.20 (2H, m), 7.40~7.55 (2H, m) | 359 (MH$^+$) |

INDUSTRIAL APPLICABILITY

The 2,3-dihydrobenzofuran derivatives of the present invention and the non-toxic salts thereof have a strong affinity for serotonin 1A receptors. Therefore, pharmaceutical compositions containing the 2,3-dihydrobenzofuran derivatives and the non-toxic salts thereof are especially useful for treating a serotonergic neuron-related disease, such as anxiety, depression, eating disorder, high blood pressure, emesis (including emesis induced by motion sickness, space sickness, dizziness and drug, etc.) and the like.

We claim:

1. A 2,3-dihydrobenzofuran derivative represented by formula (1) or a salt thereof:

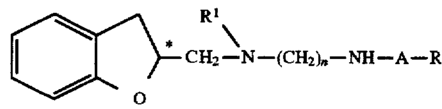

wherein $R^1$ represents a hydrogen atom or a lower alkyl group; $R^2$ represents a naphthyl group, a pyridyl group, a furyl group or a thienyl group; n is an integer of from 2 to 6; A represents a carbonyl group or a sulfonyl group; and * represents an asymmetric carbon atom.

2. The derivative or the salt thereof according to claim 1, which is selected from the group consisting of:

2-{N-[4-(1-naphthoylamino)butyl]}aminomethyl-2,3-dihydrobenzo[b]furan,
2-{N-[4-(2-naphthoylamino)butyl]}aminomethyl-2,3-dihydrobenzo[b]furan,
2-{N-[4-(4-pyridylcarbonylamino)butyl]}aminomethyl-2,3-dihydrobenzo[b]furan,
2-{N-[4-(3-pyridylcarbonylamino)butyl]}aminomethyl-2,3-dihydrobenzo[b]furan,
2-{N-[4-(2-pyridylcarbonylamino)butyl]}aminomethyl-2,3-dihydrobenzo[b]furan,
2-{N-[4-(2-thienylcarbonylamino)butyl]}aminomethyl-2,3-dihydrobenzo[b]furan,
2-{N-[4-(3-thienylcarbonylamino)butyl]}aminomethyl-2,3-dihydrobenzo[b]furan,
2-{N-[4-(2-furylcarbonylamino)butyl]}aminomethyl-2,3-dihydrobenzo[b]furan,
2-{N-[4-(3-furylcarbonylamino)butyl]}aminomethyl-2,3-dihydrobenzo[b]furan,
(+)-2-{N-[4-(2-thienylcarbonylamino)butyl]}aminomethyl-2,3-dihydrobenzo[b]furan,
(−)-2-{N-[4-(2-thienylcarbonylamino)butyl]}aminomethyl-2,3-dihydrobenzo[b]furan,
2-{N-[2-(1-naphthoylamino)ethyl]}aminomethyl-2,3-dihydrobenzo[b]furan,
2-{N-[3-(1-naphthoylamino)propyl]}aminomethyl-2,3-dihydrobenzo[b]furan,
2-{N-[4-(1-naphthylsulfonylamino)butyl]}aminomethyl-2,3-dihydrobenzo[b]furan,
2-{N-[4-(2-naphthylsulfonylamino)butyl]}aminomethyl-2,3-dihydrobenzo[b]furan,
(−)-2-{N-methyl-N-[4-(2-thienylcarbonylamino)butyl]}aminomethyl-2,3-dihydrobenzo[b]furan,
(−)-2-{N-ethyl-N-[4-(2-thienylcarbonylamino)butyl]}aminomethyl-2,3-dihydrobenzo[b]furan, and salts thereof.

3. A method for producing a 2,3-dihydrobenzofuran derivative represented by formula (1) or a salt thereof:

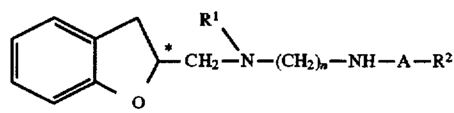

wherein $R^1$ represents a hydrogen atom or a lower alkyl group; $R^2$ represents a naphthyl group, a pyridyl group, a furyl group or a thienyl group; n is an integer of from 2 to 6; A represents a carbonyl group or a sulfonyl group; and * represents an asymmetric carbon atom, which comprises reacting a compound represented by formula (2):

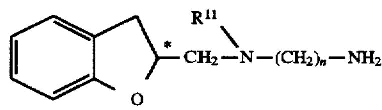

wherein $R^{11}$ represents an amino-protecting group or a lower alkyl group; n is an integer of from 2 to 6; and * represents an asymmetric carbon atom, with a compound represented by formula (3):

$$X—A—R^2 \quad (3)$$

wherein $R^2$ represents a naphthyl group, a pyridyl group, a furyl group or a thienyl group; A represents a carbonyl group or a sulfonyl group; and X represents a leaving atom or group.

wherein when $R^{11}$ in formula (2) is an amino-protecting group, a product obtained by the reaction of said compound represented by formula (2) with said compound represented by formula (3) is subsequently subjected to a treatment for removing said amino-protecting group so that a hydrogen atom is substituted therefor.

4. A pharmaceutical composition which comprises a therapeutically effective amount of a 2,3-dihydrobenzofuran derivative represented by formula (1) or a non-toxic salt thereof:

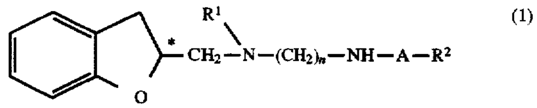

wherein $R^1$ represents a hydrogen atom or a lower alkyl group; $R^2$ represents a naphthyl group, a pyridyl group, a furyl group or a thienyl group; n is an integer of from 2 to 6; A represents a carbonyl group or a sulfonyl group; and * represents an asymmetric carbon atom, and at least one pharmaceutically acceptable carrier, diluent or excipient.

5. The pharmaceutical composition according to claim 4, which is for treating a serotonergic neuron-related disease.

6. The pharmaceutical composition according to claim 4 or 5, wherein said 2,3-dihydrobenzofuran derivative or said nontoxic salt thereof is at least one compound selected from the group consisting of:

2-{N-[4-(1-naphthoylamino)butyl]}aminomethyl-2,3-dihydrobenzo[b]furan,

2-{N-[4-(2-naphthoylamino)butyl]}aminomethyl-2,3-dihydrobenzo[b]furan,

2-{N-[4-(4-pyridylcarbonylamino)butyl]}aminomethyl-2,3-dihydrobenzo[b]furan,

2-{N-[4-(3-pyridylcarbonylamino)butyl]}aminomethyl-2,3-dihydrobenzo[b]furan,

2-{N-[4-(2-pyridylcarbonylamino)butyl]}aminomethyl-2,3-dihydrobenzo [b]furan,

2-{N-[4-(2-thienylcarbonylamino)butyl]}aminomethyl-2,3-dihydrobenzo[b]furan,

2-{N-[4-(3-thienylcarbonylamino)butyl]}aminomethyl-2,3-dihydrobenzo[b]furan,

2-{N-[4-(2-furylcarbonylamino)butyl]}aminomethyl-2,3-dihydrobenzo[b]furan,

2-{N-[4-(3-furylcarbonylamino)butyl]}aminomethyl-2,3-dihydrobenzo[b]furan, (+)-2-{N-[4-(2-thienylcarbonylamino)butyl]}aminomethyl-2,3-dihydrobenzo[b]furan, (−)-2-{N-[4-(2-thienylcarbonylamino)butyl]}aminomethyl-2,3-dihydrobenzo[b]furan, 2-{N-[2-(1-naphthoylamino)ethyl]}aminomethyl-2,3-dihydrobenzo[b]furan, 2-{N-[3-(1-naphthoylamino)propyl]}aminomethyl-2,3-dihydrobenzo[b]furan, 2-{N-[4-(1-naphthylsulfonylamino)butyl]}aminomethyl-2,3-dihydrobenzo[b]furan, 2-{N-[4-(2-naphthylsulfonylamino)butyl]}aminomethyl-2,3-dihydrobenzo[b]furan, (−)-2-{N-methyl-N-[4-(2-thienylcarbonylamino)butyl]}aminomethyl-2,3-dihydrobenzo[b]furan, (−)-2-{N-ethyl-N-[4-(2-thienylcarbonylamino)butyl]}aminomethyl-2,3-dihydrobenzo[b]furan, and salts thereof.

7. A method for treating a serotonergic neuron-related disease, which comprises administering to a patient suffering from a serotonergic neuron-related disease a pharmaceutical composition comprising a therapeutically effective amount of a 2,3-dihydrobenzofuran derivative represented by formula (1) or a non-toxic salt thereof:

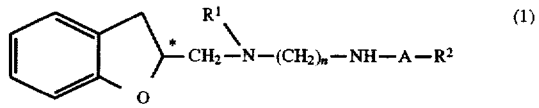

wherein $R^1$ represents a hydrogen atom or a lower alkyl group; $R^2$ represents a naphthyl group, a pyridyl group, a furyl group or a thienyl group; n is an integer of from 2 to 6; A represents a carbonyl group or a sulfonyl group; and * represents an asymmetric carbon atom, and at least one pharmaceutically acceptable carrier, diluent or excipient.

8. The method according to claim 7, wherein said 2,3-dihydrobenzofuran derivative or said non-toxic salt thereof is at least one compound selected from the group consisting of:

2-{N-[4-(1-naphthoylamino)butyl]}aminomethyl-2,3-dihydrobenzo[b]furan,

2-{N-[4-(2-naphthoylamino)butyl]}aminomethyl-2,3-dihydrobenzo[b]furan,

2-{N-[4-(4-pyridylcarbonylamino)butyl]}aminomethyl-2,3-dihydrobenzo[b]furan,

2-{N-[4-(3-pyridylcarbonylamino)butyl]}aminomethyl-2,3-dihydrobenzo[b]furan,

2-{N-[4-(2-pyridylcarbonylamino)butyl]}aminomethyl-2,3-dihydrobenzo[b]furan,

2-{N-[4-(2-thienylcarbonylamino)butyl]}aminomethyl-2,3-dihydrobenzo[b]furan,

2-{N-[4-(3-thienylcarbonylamino)butyl]}aminomethyl-2,3-dihydrobenzo[b]furan,

2-{N-[4-(2-furylcarbonylamino)butyl]}aminomethyl-2,3-dihydrobenzo[b]furan,

2-{N-[4-(3-furylcarbonylamino)butyl]}aminomethyl-2,3-dihydrobenzo[b]furan, (+)-2-{N-[4-(2-thienylcarbonylamino)butyl]}aminomethyl-2,3-dihydrobenzo[b]furan, (−)-2-{N-[4-(2-thienylcarbonylamino)butyl]}aminomethyl-2,3-dihydrobenzo[b]furan, 2-{N-[2-(1-naphthoylamino)ethyl]}aminomethyl-2,3-dihydrobenzo[b]furan, 2-{N-[3-(1-naphthoylamino)propyl]}aminomethyl-2,3-dihydrobenzo[b]furan, 2-{N-[4-(1-naphthylsulfonylamino)butyl]}aminomethyl-2,3-dihydrobenzo[b]furan, 2-{N-[4-(2-naphthylsulfonylamino)butyl]}aminomethyl-2,3-dihydrobenzo[b]furan, (−)-2-{N-methyl-N-[4-(2-thienylcarbonylamino)butyl]}aminomethyl-2,3-dihydrobenzo[b]furan, (−)-2-{N-ethyl-N-[4-(2-thienylcarbonylamino)butyl]}aminomethyl-2,3-dihydrobenzo[b]furan, and salts thereof.

* * * * *